United States Patent
Brolaski et al.

(10) Patent No.: US 7,459,548 B2
(45) Date of Patent: Dec. 2, 2008

(54) KITS AND PROCESSES FOR REMOVING CONTAMINANTS FROM NUCLEIC ACIDS IN ENVIRONMENTAL AND BIOLOGICAL SAMPLES

(75) Inventors: Mark N. Brolaski, Encinitas, CA (US); Raveendran J. Venugopal, San Diego, CA (US); David Stolow, San Diego, CA (US)

(73) Assignee: Mo Bio Laboratories, Inc., Carlsbad, CA (US)

( * ) Notice: Subject to any disclaimer, the term of this patent is extended or adjusted under 35 U.S.C. 154(b) by 293 days.

(21) Appl. No.: 11/134,849

(22) Filed: May 20, 2005

(65) Prior Publication Data

US 2005/0282202 A1    Dec. 22, 2005

Related U.S. Application Data

(60) Provisional application No. 60/574,179, filed on May 24, 2004, provisional application No. 60/573,358, filed on May 21, 2004.

(51) Int. Cl.
*C07H 21/00* (2006.01)
(52) U.S. Cl. .................. 536/25.41; 536/25.42
(58) Field of Classification Search ........................ None
See application file for complete search history.

(56) References Cited

U.S. PATENT DOCUMENTS

| | | | |
|---|---|---|---|
| 3,002,960 A | 10/1961 | Kolodny | |
| 3,316,181 A | 4/1967 | Sackis | |
| 3,374,143 A | 3/1968 | Stephenson | |
| 3,686,109 A | 8/1972 | Aldrich et al. | |
| 3,692,673 A | 9/1972 | Hoke | |
| 4,010,131 A | 3/1977 | Phillips et al. | |
| 4,147,681 A | 4/1979 | Lim et al. | |
| 4,451,628 A | 5/1984 | Dammann | |
| 4,565,635 A | 1/1986 | Le Du et al. | |
| 4,683,195 A | 7/1987 | Mullis et al. | |
| 4,683,202 A | 7/1987 | Mullis | |
| 4,693,830 A | 9/1987 | Thornton et al. | |
| 4,695,453 A | 9/1987 | Tuominen et al. | |
| 4,702,844 A | 10/1987 | Flesher et al. | |
| 4,770,803 A | 9/1988 | Forsberg | |
| 4,965,188 A | 10/1990 | Mullis et al. | |
| 5,069,893 A | 12/1991 | Haase et al. | |
| 5,547,835 A | 8/1996 | Koster | |
| 5,552,316 A | 9/1996 | Savage | |
| 5,605,798 A | 2/1997 | Koster | |
| 5,637,687 A | 6/1997 | Wiggins | |
| 5,656,493 A | 8/1997 | Mullis et al. | |
| 5,691,141 A | 11/1997 | Koster | |
| 5,849,542 A | 12/1998 | Reeve et al. | |
| 5,869,242 A | 2/1999 | Kamb | |
| 5,928,906 A | 7/1999 | Koster et al. | |
| 6,027,750 A * | 2/2000 | Gautsch et al. | ............. 424/489 |
| 6,043,031 A | 3/2000 | Koster et al. | |
| 6,194,144 B1 | 2/2001 | Koster | |
| 6,268,492 B1 * | 7/2001 | Mittelstaedt et al. | ....... 536/25.4 |
| 6,613,895 B1 * | 9/2003 | Gautsch et al. | ............ 536/25.4 |

FOREIGN PATENT DOCUMENTS

| | | |
|---|---|---|
| WO | WO-96/18731 | 6/1996 |
| WO | WO03/102184 A1 * | 12/2003 |
| WO | WO2004/024283 A1 * | 3/2004 |

OTHER PUBLICATIONS

Braid et al., Journal of Microbiological Methods (2003) 52:389-393.
International Search Report for PCT/US05/17933, mailed on Aug. 4, 2006, 3 pages.
MacFarlene et al., Journal of Clinical Laboratory Analysis (1997) 11:132-139.
Ait Akbour et al., J. Colloid Interf. Sci. (2002) 253:1-8.
Alvarez-Puebla et al., Langmuir. (2004) 20:3257-3264.
Franchi et al., Orig. Life Evol. Biosph. (2003) 33:1-16.
Greaves et al., Soil Biol. Biochem. (1970) 2:257-268.
Greaves et al., Soil Biol. Biochem. (1969) 1:317-323.
Miller and Low, Langmuir. (1990) 6:572-578.
Ochs et al., Geochim. Cosmochim. Acta (1994) 58:639-650.
Ogram et al., Environ. Sci. Technol. (1988) 22:982-984.
Podoll et al., Environ. Sci. Technol. (1987) 21:562-568.
Shainberg, Soil Sci. Soc. Am. Proc. (1966) 30:700-706.

* cited by examiner

*Primary Examiner*—Shaojia Anna Jiang
*Assistant Examiner*—L. E. Crane
(74) *Attorney, Agent, or Firm*—Morrison & Foerster LLP

(57) ABSTRACT

The invention provides methods for removing a contaminant or inhibitor from a nucleic acid-comprising sample, wherein the contaminant or inhibitor inhibits the amplification or hybridization of the nucleic acid in the sample, or inhibits an enzymatic reaction utilizing the nucleic acid in the sample, the method comprising the steps of: (a) providing a reaction mixture comprising the sample, a chaotropic agent, ammonium acetate or an equivalent, and a detergent, (b) isolating the nucleic acid and remaining contaminants and inhibitors from the reaction mixture in a supernatant; and (c) contacting the nucleic acid supernatant with a flocculant resulting in the further removal of the contaminant or the inhibitor from the supernatant. The invention also provides kits that comprise the components necessary to carry out the method.

48 Claims, 4 Drawing Sheets

N P 1 2 3 4 5 6 7 8

C.  N P 1 2 3 4 5 6 7 8

Fragment

Primers

| | Soil Type 1 | | | Soil Type 2 | | | Soil Type 3 | | |
|---|---|---|---|---|---|---|---|---|---|

Volume Loaded (μl)   15  5  5   15  5  5   15  5  5

Volume Eluted (ml)   M   8 ml  1*  1^   8 ml  1*  1^   8 ml  1*  1^

*Before Purification  /  ^After Purification

| | Controls | Soil type 4 | Soil type 5 | Soil type 6 |
|---|---|---|---|---|

Volume Eluted (ml)   −  +   8  1.0*  1.0^    8  1.0*  1.0^    8  1.0*  1.0^

M   1   2   3   4   5   6   7   8   9   10  11  12  13

→ 600

→ 1200 bp

KITS AND PROCESSES FOR REMOVING CONTAMINANTS FROM NUCLEIC ACIDS IN ENVIRONMENTAL AND BIOLOGICAL SAMPLES

RELATED APPLICATIONS

This application claims the benefit of priority of U.S. Provisional Patent Application Ser. No. ("U.S. Ser. No.") 60/574,179, filed May 24, 2004, and U.S. Ser. No. 60/573,358, filed May 21, 2004. Each of the aforementioned applications are explicitly incorporated herein by reference in their entirety and for all purposes.

FIELD OF THE INVENTION

The invention provides methods and compositions, e.g., kits, for removing contaminants from nucleic acids in a sample, e.g., environmental or biological samples such as soil, food, plant, animal, microorganism or water samples. The invention provides methods and compositions, e.g., kits, for isolating nucleic acids from samples, including environmental or biological samples such as soil, food, plant, animal, microorganism or water samples. The invention relates to methods and compositions for detecting organisms, e.g., microorganisms, in a sample, e.g., an environmental or a biological sample. The nucleic acids isolated using the kits and methods of the invention are useful for performing a variety of processes applicable to agriculture, forensics, zoology and combating bioterrorism. For example, these nucleic acids are useful in the areas of molecular biological applications, including, for example, analytical, cloning, diagnostic and detection in the fields of agriculture, horticulture, forestry, forensics, biological research, organism and sample composition identification and characterization.

BACKGROUND

Nucleic acid sequences have a wide variety of applications in the field of molecular biology. They are a valuable tool in many analytical and application techniques used in the field of molecular biology, health and medicine (gene therapy, diagnostics, recombinant protein expression), bioterrorism (agent detection and analysis), forensics, space science, and food science. Some examples of these techniques include genotyping microorganisms, DNA fingerprinting plants and animals, detecting pathogens and beneficial microorganisms in soils, water, plants and animals, forensic identification of biological samples and environmental samples contaminated with different biological entities. All these techniques are based on identifying a specific sequence of nucleic acid in either a biological sample, such as a microorganism, plant tissues or animal tissues, or in any environment capable of supporting life. Identifying target nucleic acid sequences directly in biological samples and in environmental samples has the advantages of speed, accuracy, high-throughput and a low limit of detection to picogram or femtogram quantities of nucleic acids. The target nucleic acid sequence, in order to be used as a diagnostic tool in such applications, should be free of contaminants that inhibit PCR and other downstream applications. These contaminants are often from the groups that include polyphenols, polysaccharides and humic substances.

The field of nucleic acid extraction and subsequent amplification of this DNA by polymerase chain reaction (PCR) has revolutionized the rapid analysis of genetic composition of several ecosystems. Methods and kits are available for isolating genomic DNA from a wide range of biological entities, and from the environment in which these living entities dwell. The polymerase chain reaction (PCR) is a very powerful and sensitive analytical technique with applications in many diverse fields, including molecular biology, clinical diagnosis, forensic analysis, and population genetics. However, the success rate in soil and plant genomic analysis has been relatively slow due to the poor quality of DNA isolated. In plant genomic DNA analysis, the DNA is invariably co-extracted with other plant components such as polyphenols and polysaccharides which inhibit PCR applications.

In the field of soil ecosystems, nucleic acid extraction methods suffer from compounded inefficiencies of DNA sorption to soil surfaces and co-extraction of enzymatic inhibitors from soils. Both the clay and organic fractions of soil affect DNA isolation and purification. Clay has a tendency to bind DNA adsorptively, whereas humic polymers found in the organic fraction tend to co-purify with DNA during the extraction procedure. The higher the montmorillonitic clay and organic matter content, the higher the buffering capacity of the soil system and also greater the amount of DNA adsorbed to the soil particles. Thus methods developed for a particular soil type with a clay:organic ratio may not work for any other soil type with different clay:organic ratio. It has been previously reported that phenol extraction of DNA contaminated with humic substances resulted in lowering the DNA recovery efficiency. Compost may have a variety of additional organic compounds that may co-purify with DNA and inhibit enzymatic manipulations of the DNA. An additional concern when isolating microbial DNA from compost is that plant material in various stages of decomposition may be present in significant concentrations in compost.

Studies of higher organisms such as fungi, plants and animals, direct nucleic acid isolations are still plagued with quality issues. In cyanobacteria, fungi, algae and plants, pigments and cell wall components such as chitins and polysaccharides will inhibit PCR. These cell types are rich in endo— and exonucleases and contain photosynthetic pigments, which can inhibit enzymatic reactions, especially reverse transcription and PCR.

The nature of the contaminants in crude nucleic acid preparations from soils and sediments and their interactions with DNA and RNA are not well understood. Most frequently these contaminants are considered to be humic and fulvic acids and a heterogeneous mixture of phenolic polymers and oligomers. Humic substances are formed when microbes degrade plant residues and are stabilized to degradation by covalent binding of their reactive sites to metal ions and clay minerals. Humic substances consist of polycyclic aromatics to which saccharides, peptides, and phenols are attached. The predominant types of humic substances in soils are humic acids (HA, molecular weight of 300 kDa and greater) and fulvic acids (FA, molecular weight of as low as 0.1 kDa). Humic acids are soluble in alkaline pH and precipitate with hydrochloric or sulphuric acids at pH 1.0 to 2.0, while fulvic acids remain in solution even at acidic pH (Stevenson, 1994). Most frequently, DNA extracts from soils showing brown coloration are indicative of contamination with humic like substances. These brown compounds cannot be easily removed from DNA extracts. Solvent extraction of crude DNA extracts with solvents such as phenol, diethyl ether, acetone, methanol and ethanol were not successful in removing the brown coloration, and the DNA was still discolored and resistant to digestion by restriction endonucleases. Some of these compounds also appear to co-migrate with DNA during CsCl-ethidium bromide isopycnic ultracentrifugation, resulting in light brown coloration of the recovered DNA.

These observations imply an intimate association between the contaminants and DNA. While the nature of the association between contaminating compounds and DNA has not been elucidated, the reversible and irreversible binding of polyphenols, such as tannins, to proteins is well understood.

Direct extraction of total nucleic acid from soils or sediments usually results in co-extraction of other soil components, mainly humic acids or other humic substances, which negatively interfere with DNA transforming and detecting processes. It has been reported that these substances inhibit restriction endonucleases and Taq polymerase, the key enzyme of PCR, and decrease efficiencies in DNA-DNA hybridizations. Separation of humic substances from DNA usually involves time-consuming and tedious steps. To circumvent this, size-exclusion chromatography and the use of polyvinylpolypyrrolidone spin columns have been widely used. Size-exclusion chromatography includes the use of SEPHADEX G-200™ or MICROSPIN S-400 HR™, while water-insoluble PVPP and water-soluble polyvinylpyrrolidone (PVP) as humic acid-binding agents have also been reported.

SUMMARY OF THE INVENTION

The invention provides methods and compositions, e.g., kits, for removing contaminants from nucleic acids in a sample, e.g., environmental or biological samples such as soil, food (e.g., for inspections), plant, animal, microorganism or water samples. In one aspect, the methods and compositions of the invention are used to remove those contaminants in the sample that can impede or inhibit a nucleic acid amplification reaction. Thus, the methods and compositions of the invention are used to increase the accuracy and/or efficiency of nucleic acid (e.g., RNA-DNA or DNA-DNA) hybridization reactions, including amplification reactions such as PCR and RT-PCR). The invention also provides methods and compositions, e.g., kits, for isolating nucleic acids from samples, including environmental or biological samples. In one aspect, the invention is used with flocculating materials in purifying DNA and RNA from a wide variety of samples, e.g., biological or environmental samples, such as soil, food (e.g., meat, vegetables and the like; e.g., for determining contamination of food, including meat, seafood, vegetables, fruit and the like), plant, animal, microorganism or water samples. The methods and compositions of the invention can be used for isolating nucleic acids from environmental and biological samples free from contaminating substances that inhibit PCR, RT-PCR and other downstream applications in molecular biology. In one aspect, the method comprises contacting the flocculant with the contaminants present along with the nucleic acids at a specified step in the protocol. The method is scaleable and exemplary embodiments include integrating the method into a nucleic acid purification process and applying the method to remove contaminants from existing purified nucleic acids. The method has applications in agriculture, diagnostics, horticulture, forestry, forensics, combating bioterrorism and other areas where contaminant-free nucleic acid is used.

In one aspect, the present invention is directed to methods and kits for obtaining nucleic acids from a wide variety of biological and environmental samples in such a way that the isolated nucleic acids are free of contaminating materials, mainly polyphenols, polysaccharides and humic substances. An exemplary embodiment of this invention is the use of a flocculating material at a specific step in the protocol where the use of the flocculating material improves significantly the final purity of the isolated DNA and RNA as opposed to the existing art in the use of flocculating materials. We have provided examples of the use of this invention in the purification processes involved in obtaining DNA and RNA from soils and other environmental samples.

In one aspect, the invention provides methods for isolating a nucleic acid from a sample comprising: (a) releasing a nucleic acid into the sample medium; (b) contacting the sample medium with at least one flocculant after the nucleic acid is released from the sample; and (c) separating the nucleic acid from the flocculant, wherein optionally the method further comprises purifying the nucleic acid after step (c). In one aspect, the invention provides methods for isolating a nucleic acid from a sample comprising: (a) releasing a nucleic acid into the sample medium and comprising a step of adding a first flocculant to the processed, unprocessed, preserved, freshly isolated, crude or unrefined sample medium; (b) contacting the sample medium with a second flocculant after the nucleic acid is extracted from the processed, unprocessed, preserved, freshly isolated, crude or unrefined sample; and (c) separating the nucleic acid from the second flocculant, wherein optionally the method further comprises purifying the nucleic acid after step (c).

The invention provides methods and kits for removing contaminants from a nucleic acid-comprising sample, wherein the contaminants inhibit (partially or completely) amplification or hybridization of nucleic acids in the sample, the method comprising the steps of: (a) contacting the nucleic acid-comprising sample with at least one flocculant to form a flocculant precipitate; and (b) separating the nucleic acid from the flocculant precipitate, wherein in one aspect (optionally) the method further comprises purifying or isolating the nucleic acid after step (b), and in one aspect (optionally) the sample is an unprocessed, preserved, freshly isolated, crude or unrefined sample, or, the sample is broken up, denatured or disrupted before contacting with the flocculant. The invention also provides methods and kits for removing contaminants from a nucleic acid-comprising sample, wherein the contaminants inhibit (partially or completely) amplification or hybridization of nucleic acids in the sample, the method comprising the steps of: (a) contacting the nucleic acid-comprising sample with at least a first flocculant to form a first flocculant precipitate, wherein in one aspect (optionally) the sample is an unprocessed, preserved, freshly isolated, crude or unrefined sample, or, the sample is broken up, denatured or disrupted before contacting with the flocculant; (b) separating the nucleic acid from the first flocculant precipitate; (c) contacting the nucleic acid with a second flocculant to form a flocculant precipitate; and (d) separating the nucleic acid from the second flocculant precipitate, wherein in one aspect (optionally) the method or kit further comprises purifying the nucleic acid after step (d). In one aspect, any method or kit of the invention can also be used to remove one or more contaminant(s) from a nucleic acid-comprising sample to facilitate a desired enzymatic or detection reaction, e.g., a ligase or phosphorylase reaction (e.g., to remove a composition in the sample that slows, inhibits or otherwise interferes with the desired enzymatic or detection reaction or process).

The invention provides methods and kits for selectively removing compounds from a nucleic acid-comprising sample, wherein the compounds inhibit (partially or completely) amplification or hybridization of nucleic acids in the sample, the method comprising the steps of: (a) contacting the nucleic acid-comprising sample with at least a first flocculant to form a flocculant precipitate, wherein in one aspect (optionally) the sample is an unprocessed, preserved, freshly isolated, crude or unrefined sample, or, the sample is broken up, denatured or disrupted before contacting with the at least a first flocculant; (b) separating the nucleic acid from the first flocculant precipitate; (c) contacting the nucleic acid with a second flocculant to form a second flocculant precipitate; and (d) separating the nucleic acid from the second flocculant precipitate, wherein in one aspect (optionally) the method or kit further comprises purifying the nucleic acid after step (d), and in one aspect (optionally) the sample is treated or disrupted before the at least one flocculant is added to the sample. The invention also provides methods and kits for selectively removing compounds from a nucleic acid-comprising sample, wherein the compounds inhibit (partially or completely) amplification or hybridization of nucleic acids in the sample, the method comprising the steps of: (a) processing the sample to break up, denature or disrupt the sample before contacting it with a flocculant, wherein the processing treatment comprises mixing or contacting the sample with a solution comprising a chaotropic agent (e.g., guanidium chloride), a detergent (e.g., SDS, see further examples, below), a buffer, a homogenizing agent or a combination thereof; (b) contacting the nucleic acid-comprising sample with at least a first flocculant to form a flocculant precipitate, wherein in one aspect (optionally) the contacting comprises mixing or vortexing the flocculant and the sample; (c) separating a nucleic acid-comprising solution from the first flocculant precipitate, wherein in one aspect (optionally) the separating comprises centrifuging the flocculant and the sample and harvesting a nucleic acid-comprising supernatant; (d) contacting the nucleic acid-comprising solution with a second flocculant to form a second flocculant precipitate; and (e) separating the nucleic acid from the second flocculant precipitate, wherein in one aspect (optionally) the separating comprises centrifuging the flocculant and the sample and harvesting a nucleic acid-comprising supernatant; wherein in one aspect (optionally) the method or kit further comprises purifying the nucleic acid after step (e). In one aspect, any method or kit of the invention can also be used to remove one or more contaminant(s) from a nucleic acid-comprising sample to facilitate a desired enzymatic or detection reaction or process, e.g., a ligase or phosphorylase reaction (e.g., to remove a composition in the sample that slows, inhibits or otherwise interferes with the desired enzymatic or detection reaction).

The invention provides methods and kits for amplifying, hybridizing, isolating or purifying from a nucleic acid-comprising sample, the method comprising the steps of: (a) processing the sample to break up, denature or disrupt the sample before contacting it with a flocculant, wherein the processing treatment comprises mixing or contacting the sample with a solution comprising a chaotropic agent, a detergent, a buffer, a homogenizing agent or a combination thereof; (b) contacting the nucleic acid-comprising sample with at least a first flocculant to form a flocculant precipitate, wherein the contacting comprises mixing or vortexing the flocculant and the sample, wherein in one aspect (optionally) the first flocculant comprises an ammonium acetate; (c) separating a nucleic acid-comprising solution from the first flocculant precipitate, wherein the separating comprises centrifuging the flocculant and the sample and harvesting a nucleic acid-comprising supernatant; (d) contacting the nucleic acid-comprising solution with a second flocculant to form a second flocculant precipitate, wherein in one aspect (optionally) the second flocculant comprises an aluminum sulfate dodecahydrate; (e) separating the nucleic acid from the second flocculant precipitate, wherein the separating comprises centrifuging the flocculant and the sample and harvesting a nucleic acid-comprising supernatant; and (f) amplifying, hybridizing, isolating or purifying the nucleic acid after step (e).

The invention provides methods and kits for purifying, isolating, hybridizing or amplifying a nucleic acid from a sample comprising: (a) releasing a nucleic acid into the sample medium; (b) contacting the sample medium with at least one flocculant after the nucleic acid is released from the sample; (c) separating the nucleic acid from the flocculant, wherein in one aspect (optionally) the method or kit further comprises purifying, hybridizing isolating or amplifying the nucleic acid after step (c).

The invention provides methods and kits for isolating a nucleic acid from a sample comprising: (a) extracting a nucleic acid from the sample; (b) contacting the nucleic acid with at least one flocculant after the nucleic acid is extracted from the sample; and (c) separating the nucleic acid from the flocculent, wherein in one aspect (optionally) the method or kit further comprises purifying the nucleic acid after step (c).

The invention provides methods and kits for purifying, isolating, amplifying or hybridizing a nucleic acid in a sample comprising: (a) extracting a nucleic acid from the sample comprising a step of adding a first flocculant to: (i) an unprocessed, preserved, freshly isolated, crude or unrefined sample, or (ii) a processed sample, wherein the processing comprises breaking up, denaturing or disrupting the sample before contacting it with the first flocculant, wherein in one aspect (optionally) the processing treatment comprises mixing or contacting the sample with a solution comprising a chaotropic agent, a detergent, a buffer, a homogenizing agent or a combination thereof, such that a flocculant precipitate and a nucleic acid-comprising supernatant is formed; (b) removing the flocculant precipitate from the nucleic acid-comprising supernatant, wherein in one aspect (optionally) the separating comprises centrifuging the sample to form a precipitate-free nucleic acid-comprising supernatant; (c) contacting the nucleic acid with a second flocculant to form a second flocculant precipitate; and (d) separating the nucleic acid from the second flocculant and flocculant precipitate, wherein in one aspect (optionally) the separating comprises centrifuging the sample to form a precipitate-free nucleic acid-comprising supernatant, and (e) purifying, isolating, amplifying or hybridizing the nucleic acid after step (d).

The invention provides methods and kits for purifying, isolating, amplifying or hybridizing a nucleic acid in a sample comprising: (a) extracting a nucleic acid from the sample comprising a step of adding a first flocculant to: (i) an unprocessed, preserved, freshly isolated, crude or unrefined sample, or (ii) a processed sample, wherein the processing comprises breaking up, denaturing or disrupting the sample before contacting it with the first flocculent, and the processing treatment comprises mixing or contacting the sample with a solution comprising a chaotropic agent, a detergent, a buffer, a homogenizing agent or a combination thereof, such that a flocculant precipitate and a nucleic acid-comprising supernatant is formed, wherein in one aspect (optionally) the first flocculant comprises ammonium acetate; (b) removing the flocculant precipitate from the nucleic acid-comprising supernatant, wherein the separating comprises centrifuging the sample to form a precipitate-free nucleic acid-comprising supernatant; (c) contacting the nucleic acid with a second flocculant to form a second flocculant precipitate, wherein in one aspect (optionally) the second flocculant comprises aluminum ammonium sulfate dodecahydrate; and (d) separating the nucleic acid from the second flocculant and flocculant precipitate, wherein the separating comprises centrifuging the sample to form a precipitate-free nucleic acid-comprising supernatant, and (e) purifying, isolating, amplifying or hybridizing the nucleic acid after step (d).

In one aspect of a method or a kit of the invention, the flocculant comprises a cationic chemical substance, an anionic chemical substance, a zwitterionic chemical substance, a non-charged chemical substance or a combination thereof. In one aspect, the cationic, anionic, zwitterionic or non-charged substance comprises a quaternary ammonium or tertiary amine containing polymer. In one aspect, the flocculant is selected from the group consisting of ammonium acetate, magnesium chloride ($MgCl_2$), ferric chloride ($FeCl_3$), a salt of iron, a salt of aluminum, calcium chloride ($CaCl_2$), a polyacrylamide, aluminum ammonium sulfate, derivatives thereof, and a combination thereof.

The methods of the invention can further comprise detecting or characterizing a purified, isolated, amplified or hybridized nucleic acid. In one aspect, the nucleic acid is detected by a nucleic acid amplification reaction, immobilization on a solid support, hybridization, restriction enzyme digestion, RNase digestion, reverse transcription, DNAse digestion, electrophoresis, chromatography or a combination thereof. In one aspect the nucleic acid amplification reaction comprises a detection method, a polymerase chain reaction (PCR), a reverse transcription, a rolling circle replication, a ligase-chain reaction, a nucleic acid labeling or tagging reaction, derivative methods thereof or a combination thereof.

The methods of the invention can further comprise identifying an organism or nucleic acid component in the sample. The organism can be identified by identifying or characterizing the purified, isolated, amplified or hybridized nucleic acid. The detected organism or nucleic acid component can be derived from a microorganism, an animal, a plant, an insect, a yeast, a virus, a phage, a nematode, a bacteria or a fungi. The bacteria detected can comprise a gram positive or a gram negative bacteria.

In one aspect the sample comprises an environmental or a biological sample. The environmental or biological sample can comprise a sample derived from an animal, animal remains, a food, a microorganism, a plant or its components, soil, sediment, rock, reef, sludge, compost, decomposing biological matter, a biopsy, a histological sample, a semen sample, a blood or saliva sample, any body fluid sample, a hair sample, a skin sample, a fecal sample, archaeological remains, a peat bog, compost, oil, water, terrestrial water or subterranean water, atmospheric and industrial water, dust, urban dust, commercial potting mixtures or soil amendments, deep sea vents, or air, wherein in one aspect (optionally) the sample is processed by mechanical filtering, sedimentation or centrifugation.

In any method or kit of the invention, the nucleic acid comprises an RNA (e.g., mRNA, tRNA, rRNA, iRNA) or a DNA or a combination thereof.

Any method or kit of the invention can comprise the step of extracting a nucleic acid from the sample, comprising a step of homogenizing a processed, an unprocessed, freshly isolated, preserved, crude or unrefined sample. In one aspect, the sample is homogenized by contacting the sample with a mechanical force, shear force, sound vibration, mechanical vibration or a vortex or vortex adapter (e.g., Vortex Adapter, MoBio, Carlsbad, Calif.), wherein in one aspect (optionally) the mechanical or shear force comprises used of a glass, a ceramic, a metal, a mineral or a plastic material or a combination thereof, and in one aspect (optionally) the material is in the form of a bead. In one aspect, the method or kit further comprises adding a homogenizing material to the sample for the homogenizing step, wherein in one aspect (optionally) the homogenizing material comprises a glass, a ceramic, a metal, a mineral, a plastic or a combination thereof.

In one aspect, the nucleic acid can extracted from the sample by a step comprising contacting the sample with a liquid or a composition comprising a detergent or a surfactant or a combination thereof. In one aspect, the detergent can be selected from the group consisting of sodium dodecyl sulfate (SDS), sarkosyl, sodium lauryl sarcosinate, cetyltrimethyl ammonium bromide (CTAB), cholic acid, deoxycholic acid, benzamidotaurocholate (BATC), octyl phenol polyethoxylate, polyoxyethylene sorbitan monolaurate, tert-octylphenoxy poly(oxyethylene)ethanol, 1,4-piperazinebis-(ethanesulfonic acid), N-(2-acetamido)-2-aminoethanesulfonic acid, polyethylene glycoltert-octylphenyl ether (Triton®X-100), (1,1,3,3-tetramethylbutyl)phenyl-polyethylene glycol (Triton®X-114) and a combination thereof. In one aspect, the nucleic acid is contacted with the flocculant after separating a substantial amount of the detergent from the nucleic acid.

In one aspect, the flocculant does not substantially precipitate the nucleic acid. In one aspect, the flocculant precipitates some but not all of the nucleic acid (e.g., at least 50%, 60%, 70%, 75%, 80%, 85%, 90%, 95%, 96%, 97%, 98%, 99%, or more of the nucleic acid is lost in the precipitate, or, alternatively 50%, 60%, 70%, 75%, 80%, 85%, 90%, 95%, 96%, 97%, 98%, 99%, or more of the nucleic acid remains in a supernatant and is recovered, amplified, purified or hybridized and the like). In one aspect, the flocculant substantially precipitates the nucleic acid. In one aspect, the flocculant precipitates one or more substances selected from the group consisting of a humic acid, a fulvic acid and humin. In one aspect, the flocculant is separated from the nucleic acid by contacting the flocculant and nucleic acid with a solid support under conditions in which the nucleic acid selectively binds to the solid support.

In one aspect, the solid support comprises or consists of a glass, an agarose, a plastic, a silica, a polyacrylamide, a hydrogel or a gel.

In one aspect, the methods or kits or the invention can further comprise amplifying the nucleic acid or a portion thereof after the step of separating the flocculant or the flocculant precipitate from the nucleic acid (after the step of separating either the first and/or the second flocculant precipitate). In one aspect, the nucleic acid is amplified using a polymerase chain reaction (PCR) procedure, rolling circle replication, ligase-chain reaction or derivative methods thereof. In one aspect, the nucleic acid separated from the flocculant or the flocculant precipitate is substantially free of a substance that inhibits a polymerase chain reaction procedure.

In one aspect, the nucleic acid comprises an RNA, and the RNA is reverse transcribed after the flocculant or the flocculant precipitate is separated from the nucleic acid. In one aspect, the nucleic acid is contacted with a restriction enzyme after the flocculant or the flocculant precipitate is separated from the nucleic acid.

In one aspect, the nucleic acid (e.g., isolated, purified or amplified by or after using a method or kit of the invention) is analyzed by mass spectrometry; agarose, capillary or polyacrylamide electrophoresis; hybridization; an array; a microarray; an enzymatic reaction; a fluorescent assay; a radioactive assay; a chromatographic assay; or, a combination thereof, after the flocculant or the flocculant precipitate is separated from the nucleic acid. In one aspect, the nucleic acid is contacted with one or more oligonucleotides after the flocculant or the flocculant precipitate is separated from the nucleic acid. In one aspect, one or more of the oligonucleotides hybridizes to the nucleic acid. In one aspect, a nucleic acid (e.g., isolated, purified or amplified by or after using a method or kit of the invention) is immobilized to a solid surface or is hybridized to a nucleic acid immobilized on a solid surface after the flocculant or the flocculant precipitate is separated from the nucleic acid.

The invention provides method or kits for post-isolation purification of a nucleic acid isolated by an existing method from an environmental or a biological sample that did not yield a detectable amplification product in a polymerase chain reaction (PCR) process, comprising (a) contacting the isolated nucleic acid with flocculant; and in one aspect (optionally) contacting the isolated nucleic acid with a second flocculant; and (c) separating the nucleic acid from the flocculant.

The invention provides method or kits for post-isolation purification or amplification of a nucleic acid extracted from an environmental or a biological sample, wherein the isolated nucleic acid does not yield a detectable amplification product in an amplification reaction, and in one aspect (optionally) the amplification reaction is a polymerase chain reaction (PCR), comprising (a) adding a sufficient amount of a first flocculant to the isolated sample to generate a flocculant precipitate and a nucleic acid-comprising supernatant; (b) removing the flocculant precipitate from the nucleic acid-comprising supernatant; and, (c) purifying or amplifying the nucleic acid from the nucleic acid-comprising supernatant. The methods can further comprise the steps of contacting the nucleic acid-comprising supernatant generated in step (b) with a second flocculant to generate a second flocculant precipitate and second nucleic acid-comprising supernatant, and the nucleic acid is purified or amplified from the second nucleic acid-comprising supernatant. The methods can further comprise contacting the isolated sample or nucleic acid, or the first or second flocculant precipitate, with a detergent. In one aspect, a substantial amount of the detergent is separated from the nucleic acid before the nucleic acid is contacted with the flocculant, or before the nucleic acid is purified or amplified.

The invention provides method or kits for releasing DNA from a sample comprising: (a) releasing a DNA from the sample comprising a step of adding a first flocculant comprising a quaternary ammonium or tertiary amine containing polymer to a processed, an unprocessed, preserved, freshly isolated, crude or unrefined sample medium, to generate a first flocculant precipitate and a first DNA-comprising supernatant, wherein in one aspect (optionally) the quaternary ammonium or tertiary amine comprises an ammonium acetate; and (b) contacting the first DNA-comprising supernatant with a second flocculant comprising a quaternary ammonium or tertiary amine to generate a second flocculant precipitate and a second DNA-comprising supernatant, wherein in one aspect (optionally) the quaternary ammonium or tertiary amine comprises an aluminum ammonium sulfate.

The invention provides method or kits for releasing RNA from a sample comprising: (a) releasing an RNA from the sample comprising a step of adding a first flocculant comprising a quaternary ammonium or tertiary amine containing polymer to an processed, unprocessed, preserved, freshly isolated, crude or unrefined sample medium, to generate a first flocculant precipitate and a first RNA-comprising supernatant, wherein in one aspect (optionally) the quaternary ammonium or tertiary amine comprises an ammonium acetate; (b) contacting the first RNA-comprising supernatant with a second flocculant comprising a quaternary ammonium or tertiary amine to generate a second flocculant precipitate and a second RNA-comprising supernatant, wherein in one aspect (optionally) the method comprises further comprises after step (b) contacting the nucleic acid with a buffer comprising phenol.

The invention provides kits for isolating a nucleic acid from a samples comprising at least one flocculant and instructions describing a method for use according to any of the methods of the invention. In one aspect of the kit, the flocculant comprises an anionic, cationic, zwitterionic or uncharged chemical substance or combination thereof, wherein in one aspect (optionally) the cationic substance comprises a quaternary ammonium or tertiary amine containing polymer. The flocculant can be selected from the group consisting of ammonium acetate, magnesium chloride ($MgCl_2$), ferric chloride ($FeCl_3$), an iron salt or an aluminum salt, calcium chloride ($CaCl_2$), a polyacrylamide, aluminum ammonium sulfate and derivatives thereof.

In one aspect the kit further comprises a detergent or a surfactant. The detergent is selected from the group consisting of sodium dodecyl sulfate (SDS), sarkosyl, sodium lauryl sarcosinate, cetyltrimethyl ammonium bromide (CTAB), cholic acid, deoxycholic acid, benzamidotaurocholate (BATC), octyl phenol polyethoxylate, polyoxyethylene sorbitan monolaurate, tert-octylphenoxy poly(oxyethylene) ethanol, polyethylene glycoltert-octylphenyl ether (Triton®X-100), (1,1,3,3-tetramethylbutyl) phenyl-polyethylene glycol (Triton®X-114) and a combination thereof.

In one aspect the kit further comprises a homogenizing material (e.g., a bead). In one aspect the kit further comprises a bead, wherein in one aspect (optionally) the bead is a homogenizing bead.

In one aspect the kit further comprises one or more solutions or buffers (e.g., Tris, MOPS, etc.) for performing a method according to any of the methods of the invention. In one aspect the kit comprises instructions describing a method for obtaining a sample for processing.

In one aspect the kit further comprises one or more vessels or containers, e.g., tube vessels (e.g., test tube, capillary, Eppendorf tube) useful for performing the method of use.

In one aspect the kit further comprises one or more oligonucleotides, and in one aspect (optionally) free nucleotides, and in one aspect (optionally) sufficient free nucleotides to carry out a PCR reaction, a rolling circle replication, a ligase-chain reaction, a reverse transcription, a nucleic acid labeling or tagging reaction, or derivative methods thereof.

In one aspect the kit further comprises at least one enzyme, wherein in one aspect (optionally) the enzyme is a polymerase. In one aspect the kit further comprises one or more oligonucleotides, free nucleotides and at least one polymerase or enzyme capable of amplifying a nucleic acid in a PCR reaction, a rolling circle replication, a ligase-chain reaction, a reverse transcription or derivative methods thereof. The one or more oligonucleotides can specifically hybridize to a nucleic acid from a microorganism, an animal, a plant, an insect, a yeast, a virus, a phage, a nematode, a bacteria or a fungi. The one or more oligonucleotides can specifically hybridize to a nucleic acid from a *Bacillus* spp., a *Clostridium* spp., a *Sporolactobacillus* spp.; a *Sporocarcina* spp.; a *Filibacter* spp.; a *Caryophanum* spp.; a *Desulfotomaculum* spp.; a *Corynebacterium* spp.; a *Micrococcus* spp.; a *Mycobacterium* spp.; a *Nocardia* spp.; a *Peptococcus* spp.; a *Peptostreptococcus* spp., or a Gram negative bacteria from a family comprising Acetobacteriaceae, Alcaligenaceae, Bacteroidaceae, Chromatiaceae, Enterobacteriaceae, Legionellaceae, Neisseriaceae, Nitrobacteriaceae, Pseudomonadaceae, Rhizobiaceae, Rickettsiaceae or Spirochaetaceae. The one or more oligonucleotides can specifically hybridize to a nucleic acid from *B. anthracis, A. globiformis, B. subtilis, C. renale, C. difficile, M. luteus,* or *R. erythropolis*.

The one or more oligonucleotides can specifically hybridize to a nucleic acid from a virus, e.g., a variola, varicella, reovirus, retroviruses, HIV, HIV-1, viral hemorrhagic fevers, Ebola, Marburg, Machupo, Lassa, Variola major, viral encephalitis, any of the pathogens listed in Table 1.

The invention provides kits for the detection of a spore or bacterial toxin comprising at least one flocculant and instructions describing a method for use according to any method of the invention, wherein the kit is used to detect organisms that produce the spore or toxin, wherein optionally the toxin is a bacterial toxin. The invention provides kits for the detection of a biohazard comprising at least one flocculant and instructions describing a method for use according to any method of the invention, wherein the kit is used to detect organisms that produce a biohazard agent, wherein optionally the biohazard agent is a bacterial toxin.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

BRIEF DESCRIPTION OF THE DRAWINGS

The following drawings are illustrative of aspects of the invention and are not meant to limit the scope of the invention as encompassed by the claims.

Like reference symbols in the various drawings indicate like elements.

DETAILED DESCRIPTION OF THE INVENTION

Figure 1:
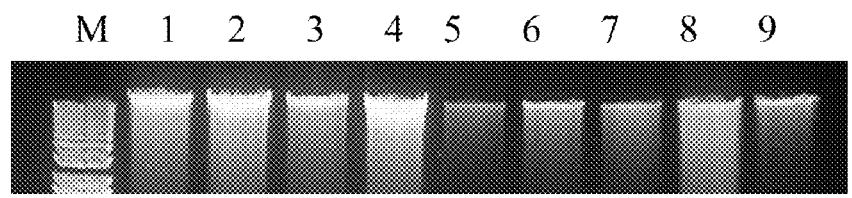
FIG. 1 illustrates an agarose gel electrophoresis showing DNA purified by an exemplary method of the invention, as described in Example 1, below.

The invention relates to methods and compositions for detecting and/or isolating nucleic acids, and/or for detecting organisms, e.g., microorganisms, in a sample, e.g., an environmental or biological samples. The invention provides methods and compositions, e.g., kits, for isolating nucleic acids from sources containing contaminating substances that interfere with use of the purified nucleic acid in subsequent applications. In one aspect, the invention provides methods and kits for purifying nucleic acids from environmental or biological samples to be free of contaminants that may or usually inhibit an enzymatic reaction, such as an amplification reaction, e.g., PCR. The biological samples include but are not limited to tissues from human, animal, plant, and the environmental samples include but are not limited to soil, sediment, sludge, decomposing biological matter, archaeological remains, peat bogs, compost and water that are terrestrial or subterranean in origin. Nucleic acids isolated using the kits and methods of the invention may be used in the areas of molecular biological application, including, for example, analytical, cloning, diagnostic and detection in the fields of agriculture, horticulture, forestry, forensics, biological research, organism and sample composition identification, characterization and combating bioterrorism.

In one aspect, the invention provides compositions and methods for isolating or extracting nucleic acids, e.g., DNA and/or RNA, by adding flocculating agents at a specific step to purify DNA and RNA from contaminants in a sample, e.g., an environmental or biological sample. In one aspect, the compositions and methods of the invention combine the properties of two reagents, ammonium acetate or equivalents, and aluminum ammonium sulfate or equivalents, to remove contaminants from DNA in (at least) two different steps. In the first step (see Example 1, below), ammonium acetate or equivalent is added to the crude environmental or biological sample (e.g., a soil mix) remove the majority of contaminants while leaving the DNA present. In this aspect, ammonium aluminum sulfate or equivalent is added next to remove the remaining contaminants, including humic substances, e.g., from soil and phenolics from plants. While the invention is not limited by any particular mechanism of action, in one aspect the interaction between the flocculating agent and the non-nucleic acid components results in a targeted mass action precipitation of the contaminating material. In one aspect, homogenization beads are used in the procedure (also noting that in one aspect a procedure of the invention does not use homogenization—which may result in a lower DNA yield as compared to using homogenization beads, or equivalent).

In one aspect, the invention provides compositions and methods for isolating or extracting DNA comprising use of two flocculating agents at separate steps in a DNA purification process to remove PCR inhibiting substances while selectively maintaining the DNA concentration. In one aspect, the invention uses flocculating agents in a step-wise approach: first using ammonium acetate or equivalent (e.g., as in step 5 in Example 1, or step 3, of Example 2, below) to remove the majority of contaminating substances and to enhance the removal efficiency of the second flocculating agent, aluminum ammonium sulfate or equivalent, added next (e.g., as in step 6 in Example 1, or step 4, of Example 2, below). In this aspect, aluminum ammonium sulfate or equivalent is used as a flocculating agent to remove humic and phenolic substances from soil and plants in a process to purify DNA from contaminants in a sample, such as an environmental or biological sample. In one aspect, the invention further comprises use of charged chemical components added to a solution to remove contaminants from DNA through flocculation during purification.

In one aspect, RNA is isolated using exemplary methods of the invention (see Example 4, below), and the invention utilizes aluminum ammonium sulfate in Step 3 (Solution SR3) as a flocculent prior to the addition of phenol (containing chloroform and isoamyl alcohol [25:24:1]). Phenol then selectively removes the remaining proteins, but more importantly for soil and plants, removes the clay and phenolics from solution. Clay is unwanted in subsequent steps for two reasons, it selectively associates with RNA and can lead to purification losses and it inhibits (either through association with RNA or interaction with enzymes) use in downstream applications.

In one aspect, exemplary methods of the invention for isolating RNA comprise: use of a flocculating agent (aluminum ammonium sulfate) to remove the majority of contaminating substances prior to adding a second reagent (phenol) to enhance the removal efficiency and selectivity of the second agent; a process to remove RT-PCR inhibiting substances using a flocculent in a process that maintains the RNA concentration; the use of phenol as a purification step to remove clay from RNA in soil samples with the intent of increasing the purification efficiency and removes contaminants; the use of chromatography as a purification method by binding RNA, DNA and contaminating substances to a solid phase matrix and selectively eluting the RNA under conditions that retain DNA and contaminating substances (humic substances in soil and phenolics in plants); the use of a charged chemical component added to solution to remove contaminants from RNA through flocculation during purification; or a combination thereof.

The invention provides compositions (e.g., kits) and methods for isolating a nucleic acid from environmental or biological samples comprising extracting a nucleic acid from the sample; and contacting the nucleic acid with a flocculant after the nucleic acid is released or extracted from the soil. In one aspect, nucleic acid is separated from the flocculant.

In one aspect, the invention provides a method for separating a nucleic acid already extracted from environmental or biological samples from contaminating substances, including polymerase chain reaction (PCR)-inhibiting substances and/or nucleic acid hybridization inhibiting substances (e.g., DNA-DNA hybridization), comprising contacting a nucleic acid extracted from environmental or biological samples with a flocculant, which alternatively can be after a substantial amount of a detergent is separated from the nucleic acid.

Also provided is a kit for isolating a nucleic acid from environmental or biological samples and a kit for purifying a nucleic acid extracted from environmental or biological samples, which comprise a flocculant and instructions describing a method for use according to any of the methods described herein for isolating the nucleic acid.

The term "soil" as used herein refers to environmental samples of soil, sediment, manure, compost, and the like, e.g., commercial potting mixtures, commercial soil amendments. The term also includes a broad range of organic carbon and nitrogen content and varying sand, silt and/or clay compositions. "Soil" includes any composition containing components commonly associated with habitable and uninhabitable areas of the earth and space, including for example varying descriptions, e.g., indoor dust, outdoor dust, dirt, mud, muck, silt, ground, compost, composting landfills at various depths. Examples of soil samples include but are not limited to landfill (e.g., 0-3 inches deep or 3-6 inches deep); late-stage compost; coffee compost; marine sediment; lake sediment; mud sediment; animal manure (e.g., horse manure); mulch, e.g., mulch top soil; the ocean floor, hillsides, mountaintops and may extend from the surface to any depth. The sample may be collected by any means using any commercially available or improvised method and tested directly. In one aspect, nucleic acid is extracted using a kit or method of the invention at the site of collection, or the sample may be stored before a nucleic acid is isolated therefrom.

By definition, "environmental" and "environmental sample", includes any environmental material, e.g., material contained in the earth and space, including space dust, airborne and waterborne locations and will include any organism, structure, and component considered alive, dead, dormant or inactive, whole, complete, undecaying and decaying that contains nucleic acid. "Environmental" and "environmental sample" include material and organisms that may be isolated from the environment as dust or suspended material collected by filtration.

The term "nucleic acid" as used herein refers to one or more nucleic acids of any kind, including single- or double-stranded forms. A nucleic acid can be DNA and in one aspect can be RNA. In practicing the methods and compositions of the invention, nucleic acid is detected and/or isolated from one or more organisms present in a sample, e.g., a soil sample, examples of which include but are not limited to bacteria (e.g., Gram positive or Gram negative), yeast, fungi, algae, viruses (e.g., HIV) and nematodes. Nucleic acid, e.g., RNA and DNA, detected or isolated using a kit or method of the invention can be from any organism, including, but not limited to viruses, bacteriophage, plasmids, spores, yeast, fingi, algae, nematodes, protozoa, eukaryotic cells, prokaryotic cells and in general, single- and multicellular forms. DNA or RNA detected or isolated using a kit or method of the invention is not necessarily located within a specific organelle among prokaryotic members, but may be found in the cytoplasm, chloroplasts, mitochondria and nuclei of eukaryotic and multicellular organisms. RNA detected or isolated using a kit or method of the invention is found in a variety of organisms, including, but not limited to viruses, eukaryotic cells, prokaryotic cells and in general, single- and multicellular forms. RNA detected or isolated using a kit or method of the invention includes forms found in a multitude of biological forms, including but not limited to, messenger RNA in protein translation, ribosomal RNA in ribosomal protein translation, transfer RNA in protein translation, small interfering RNA and micro RNA in gene regulation.

Examples of Gram negative bacteria that can be detected and/or whose nucleic acid can be isolated using the kits and methods of the invention include but are not limited to Gram negative rods (e.g., anaerobes such as bacteroidaceae (e.g., *Bacteroides fragilis*), facultative anaerobes, enterobacteriaceae (e.g., *Escherichia coli*), vibrionaceae (e.g., *Vibrio cholerae*), pasteurellae (e.g., *Haemophilus influenzae*), and aerobes such as pseudomonadaceae (e.g., *Pseudomonas aeruginosa*); Gram negative cocci (e.g., aerobes such as Neisseriaceae (e.g., *Neisseria meningitidis*) and Gram negative obligate intracellular parasites (e.g., Rickettsiae (e.g., *Rickettsia* spp.). Examples of Gram negative bacteria families that can be detected and/or whose nucleic acid can be isolated include but are not limited to Acetobacteriaceae, Alcaligenaceae, Bacteroidaceae, Chromatiaceae, Enterobacteriaceae, Legionellaceae, Neisseriaceae, Nitrobacteriaceae, Pseudomonadaceae, Rhizobiaceae, Rickettsiaceae and Spirochaetaceae.

Examples of Gram positive bacteria that can be detected and/or whose nucleic acid can be isolated using the kits and methods of the invention include but are not limited to *A. globiformis, B. subtilis, C. renale, M luteus, R. erythropolis*, Ea39, Ben-28 and *S. lividans*. Gram positive bacteria that can be detected and/or whose nucleic acid can be isolated also are in groups that include, for example, *Corynebacterium, Mycobacterium, Nocardia; Peptococcus* (e.g., *P. niger*); *Peptostreptococcus* (e.g., *Ps. anaerobius*; some species in the group form clumps and clusters; some species in the group form diplococci (the latter of which are distinguished by their ability to form butyrate); and some species in the group are capable of fermentation, reduction of nitrate, production of indole, urease, coagulase or catalase); *Ruminococcus; Sarcina; Coprococcus; Arthrobacter* (e.g., *A. globiformis, A. citreus* or *A. nicotianae*); *Micrococcus* (e.g., *M luteus* (previously known as *M. lysodeikticus*), *M. lylae, M. roseus, M. agilis, M. kristinae* and *M. halobius*); *Bacillus* (e.g., *B. anthracis, B. azotoformans, B. cereus, B. coagulans, B. israelensis, B. larvae, B. mycoides, B. polymyxa, B. pumilis, B. stearothormophillus, B. subtilis, B. thuringiensis, B. validus, B. weihenstephanensis* and *B. pseudomycoides*); *Sporolactobacillus; Sporocarcina; Filibacter; Caryophanum* and *Desulfotomaculum*. Other Gram positive bacteria that can be detected and/or whose nucleic acid can be isolated fall into the group *Clostridium*, which often include peritrichous flagellation, often degrade organic materials to acids, alcohols, $CO_2$, $H_2$ and minerals (acids, particularly butyric acid, are frequent products of clostridial fermentation), and in one aspect form ellipsoidal or spherical endospores, which may or may not swell the sporangium. Species of *Clostridium* that can be detected and/or whose nucleic acid can be isolated include psychrophilic, mesophilic or thermophilic species, saccharolytic species, proteolytic species and/or specialist species, and those that are both saccharolytic and proteolytic species. Saccharolytic species of *Clostridium* that can be detected and/or whose nucleic acid can be isolated include but are not limited to *Cl. aerotolerans, Cl. aurantibutyricum, Cl. beijerinckii, Cl. botulinum B,E,F\*, Cl. butyricum, Cl. chauvoei, Cl. difficile, Cl. intestinale, Cl. novyi A, Cl. pateurianum, Cl. saccharolyticum, Cl. septicum, Cl. thermoaceticum,* and *Cl. Thermosaccharolyticum.*

Proteolytic species of *Clostridium* that can be detected and/or whose nucleic acid can be isolated include but are not limited to *Cl. argeninense, Cl. ghoni, Cl. limosum, Cl. putrefaciens, Cl. subterminale* and *Cl. tetani.* Species that are proteolytic and saccharolytic that can be detected and/or whose nucleic acid can be isolated include but are not limited to *Cl. acetobutylicum, Cl. bifermenans, Cl. botulinum A, B, F* (prot.)\*, *Cl. botulinum C,D\*, Cl. cadaveris, Cl. haemolyticum, Cl. novyi B, C, \* Cl. perfringens, Cl. putrefaciens, Cl. sordelli* and *Cl. sporogenes.* As indicated by an asterisk, *Cl. botulinum* is subdivided into a number of types according to the serological specificities of the toxins produced. Specialist *Clostridium* species that can be detected and/or whose nucleic acid can be isolated include but are not limited to *Cl. acidiurici, Cl. irregularis, Cl. kluyveri, Cl. oxalicum, Cl. propionicum, Cl. sticklandii* and *Cl. villosum*. These specificities are based on neutralization studies. Other *Clostridium* species that can be detected and/or whose nucleic acid can be isolated include those that produce botulinum toxins.

Examples of fungi that can be detected and/or whose nucleic acid can be isolated using the kits and methods of the invention include but are not limited to *Halocyphina villosa, Hypoxylon oceanicum, Verruculina enalia, Nia vibrissa, Antennospora quadricornuta, Lulworthia* spp. and *Aigialus parvus.* Examples of algae that can be detected and/or whose nucleic acid can be isolated include but are not limited to brown algae (e.g., Phylum Phaeophycota *Dictyota* sp. (Class Phaeophyceae, Family Dictyotaceae); green algae (e.g., Phylum Chlorophycota Chaetomorpha gracilis (Class Chlorophyceae, Family Cladophoraceae); and red algae (e.g., Phylum Rhodophycota, *Catenella* sp. (Class Rhodophyceae, Family Rhabdoniaceae).

Organisms that can be detected by the kits and processes of the invention in a sample, e.g., an agricultural soil, include but are not limited to *Pseudomonas* spp., *Serratia* spp., *Bacillus* spp., *Flavobacterium* spp., Actinomycetes and fungi; in polluted soils include but are not limited to *Pseudomonas* spp. and *Xanthomonas* spp.; in marsh/sediments include but are not limited to *Escherichia* spp., *Proteus* spp., Methanogens and Actinomycetes; and in forest soils include but are not limited to Mycorrhizae, Fungi and Actinomycetes. An example of a bacterium detected in soil samples for use in combating bioterrorism using methods and kits of the invention is *Bacillus anthracis.*

Thus, the methods and kits of the invention have many medical and veterinary applications, e.g., for diagnosis, prognosis, epidemiology, inspection of contamination of materials (e.g., drugs, dressing, instruments, implants), foods (e.g., inspections of meat, vegetables, seafood, etc.), including medical and veterinary analysis of feces (including manure analysis for animals). Medical and veterinary applications include detection of soils, e.g., for bioterrorism purposes, e.g., anthrax, viruses, nematodes, and the like. Virus detection using the kits and methods of the invention can also analyze manure and soil, water, air and the like. Viruses that can be detected by kits and methods of the invention include variola, varicella, reovirus, retroviruses (e.g., HIV), viral hemorrhagic fevers (e.g., Ebola, Marburg, Machupo, Lassa), Variola major, viral encephalitis and the like, as listed in Table 1, below. The kits and methods of the invention can also be used to detect spores, toxins and biologically produced poisons, for example, by detecting *Bacillus anthracis,* anthrax spores are also detected (albeit, indirectly), detection of *Clostridium* perferinges implies presence of toxin, etc. Thus, pathogens and toxins that can be detected by kits and methods of the invention includes those listed in Table 1, below:

TABLE 1

| Disease/Type | Organism/agent | CDC Group | Specific Type | General Class | Detection Type | 1° Target |
|---|---|---|---|---|---|---|
| Anthrax | *Bacillus anthracis* | A | G+ Spore | Bacterium | DNA | Human |
| Plague | *Yersinia pestis* | A | G– Veg | Bacterium | DNA | Human |
| Tularemia | *Francisella tularensis* | A | G– Veg | Bacterium | DNA | Human |
| Brucellosis | *Brucella* spp. | B | G– Veg | Bacterium | DNA | Human |
| Glanders | *Burkholderia mallei* | B | G– Veg | Bacterium | DNA | Human |
| Melioidosis | *Burkholderia pseudomallei* | B | G– Veg | Bacterium | DNA | Human |
| Psittacosis | *Chlamydia psittaci* | B | G– Veg | Bacterium | DNA | Human |
| Q Fever | *Coxiella burnettii* | B | Gv Veg | Bacterium | DNA | Human |
| Typhus fever | *Rickettsia prowazekii* | B | Gv Veg | Bacterium | DNA | Human |

TABLE 1-continued

| Disease/Type | Organism/agent | CDC Group | Specific Type | General Class | Detection Type | 1° Target |
|---|---|---|---|---|---|---|
| Smallpox | Variola major | A | Virus | Virus | DNA | Human |
| Viral hemorrhagic fevers | Ebola | A | Filovirus | Virus | RNA | Human |
| Viral hemorrhagic fevers | Marburg | A | Filovirus | Virus | RNA | Human |
| Viral hemorrhagic fevers | Machupo | A | Arenavirus | Virus | RNA | Human |
| Viral hemorrhagic fevers | Lassa | A | Arenavirus | Virus | RNA | Human |
| Viral encephalitis | Venezuelan Equine Encephalitis | B | Alphavirus | Virus | RNA | Human |
| Viral encephalitis | Eastern Equine Encephalitis | B | Alphavirus | Virus | RNA | Human |
| Viral encephalitis | Western Equine Encephalitis | B | Alphavirus | Virus | RNA | Human |
| Botulism | *Clostridium botulinum* toxin | A | Toxin | Toxin | Protein | Human |
| Toxins | *Ricinus communis* | B | Toxin | Toxin | Protein | Human |
| Toxins | *Staph. aureus* | B | Enterotoxin B | Toxin | Protein | Human |
| Toxins | *Clostridium perferinges* toxin | B | Epsilon Toxin | Toxin | Protein | Human |

In practicing this invention, any method for extracting the nucleic acid from a sample may be used, and multiple methods are known. In one aspect, a bead beating process can be utilized in which the soil sample is contacted with beads and vibration. Vibration can be introduced by any convenient means, such as by a sonication or a vortex apparatus using a Vortex Adapter (Mo Bio Laboratories, Carlsbad, Calif.), for example. In some embodiments, extraction includes contacting the soil sample and/or nucleic acid with a detergent, examples of which include but are not limited to sodium dodecyl sulfate, sarkosyl, sodium lauryl sarcosinate, cetyltrimethylammonium bromide (CTAB, also known as hexadecyltrimethyl-ammonium bromide), cholic acid, deoxycholic acid and 4-amino-7-benzamidotaurocholic acid (BATC, also known as 2-[3a,12a-Dihydroxy-7-(4-aminobenzamido)-5b-(cholanoyl-24-amino)-ethanesulfonic acid]) polyethylene glycoltert-octylphenyl ether (Triton®X-100), (1,1,3,3-tetramethylbutyl)phenyl-polyethylene glycol (Triton®X-114).

Many methods exist in the art for exposing the nucleic acid to isolation, including breaking open the organism or organelle containing the nucleic acid in environmental and biological samples. In one aspect, liquid extraction reagents are mixed in a closed container with the sample containing nucleic acid and the mixture is shaken by hand or applied to a mixing device, exemplified by a common laboratory device known as a vortex. In one aspect, the solid sample components are then separated in a non-specific manner by centrifugation from the liquid component and the nucleic acid is extracted from the liquid portion. This process, although simple and time-saving, typically results in low nucleic acid yield and does not remove nucleic acid contaminating material that inhibits and limits further use of the nucleic acid in downstream applications. In one aspect, a disintegration process is introduced to dissociate the environmental or biological sample and disrupt the organisms and components to facilitate nucleic acid release, thereby increasing the nucleic acid yield. This process does not remove nucleic acid contaminating material but instead increases the concentration of the inhibiting material into the media. The process of disruption increases the release of humic substances in the case of environmental samples such as soils while in plants, this method increases the amount of cellular debris along with the release of nucleic acids. Disruption processes used in the methods of the invention include sonication, extrusion through a size limited opening and homogenization using mechanical shaking, often with a grinding media added to enhance sample homogenization and organism disruption. In one aspect, nucleic acid extraction is enhanced by contacting the soil sample and/or nucleic acid with a detergent, examples of which include, but are not limited to, sodium dodecyl or lauryl sulfate (SDS), sarkosyl, sodium lauryl sarcosinate, cetyltrimethylammonium bromide (CTAB, also known as hexadecyltrimethylammonium bromide), cholic acid, deoxycholic acid and 4-amino-7-benzamidotaurocholic acid (BATC, also known as 2-[3a, 12a-Dihydroxy-7-(4-aminobenzamido)-5b-(cholanoyl-24-amino)-ethanesulfonic acid]), polyethylene glycoltert-octylphenyl ether (Triton®X-100) and (1,1,3,3-tetramethylbutyl)phenyl-polyethylene glycol (Triton®X-114). This process also enhances the solubility of humic substances in soils and thus increases the amount of humic substances that is co-extracted along with nucleic acids.

In some embodiments, a hot detergent and vortex lysis procedure is utilized. In one aspect, organic extractions have been used with varying success to partition nucleic acids from proteinaceous and non-proteinaceous contaminating substances. Examples of organic extraction reagents include, but are not limited to, phenol, ether, chloroform, ethanol and isopropyl alcohol. These reagents, alone or in combination, do not completely remove contaminating substances such as humic substances but instead increase the solubility of humic substances and create conditions for them to co-purify with nucleic acids and thus inhibit useful application following purification.

In one aspect, the term "flocculant" as used in the methods and compositions of the invention refers to a substance that precipitates one or more components from solution. In one aspect, the terms "flocculant" and "precipitating reagent"

refer to a material that will combine with a dissolved and/or suspended material in a reactive or passive manner such that the combined mass of the two in a solution will reach a critical point whereby the combined material will "precipitate", i.e., become incapable of remaining suspended and "fall out" of solution. In one aspect, the flocculant can selectively precipitate certain components ("the precipitate") from solution over others. For example, the flocculant can be selected such that it does not precipitate a substantial amount of a nucleic acid from solution, but does precipitate a substantial amount of one or more substances that inhibit PCR or hybridization of an oligonucleotide to the nucleic acid. In one aspect, the flocculant precipitates a humic substance, a humic acid (the fraction of humic substances that is not soluble in water under acidic conditions (pH<2) but that is soluble at higher pH values. Humic acid can be extracted from soil by various reagents and which is insoluble in dilute acid; humic acids are the major extractable component of soil humic substances), a fulvic acid (the fraction of humic substances that is soluble in water under all pH conditions; they remain in solution after removal of humic acid by acidification and/or humin (the fraction of humic substances that is not soluble in water at any pH value and in alkali).

In one aspect, the precipitant is removed from solution by either mechanical or non-mechanical methods, resulting in a liquid solution with lowered substance content. In one aspect, flocculent and flocculating conditions are chosen to selectively precipitate certain components from solution over others. For example, in one aspect, the flocculant in the current invention is selected and introduced in the purification process in a unique way such that its interaction with soil debris and detergent is significantly induced. Thus it does not precipitate a substantial amount of a nucleic acid from solution, but does precipitate a substantial amount of one or more nucleic acid contaminating substances that inhibit, for example, PCR and RT-PCR, hybridization of an oligonucleotide to the nucleic acid or restriction (enzyme) digesting nucleic acid to produce intermediate fragments. Humic substances dominate natural environments as polymers with a broad molecular weight distribution and high chemical heterogeneity. Dissociation of humic acid (HA) functional groups results in the net negative charge of macromolecules in a wide pH range, and determines the high affinity of humics towards complex formation, as well as the high stability of humic colloids in natural ecosystems.

In alternative aspects, flocculant used to practice the invention, e.g., used in the methods and kits of the invention, comprise ionically charged (e.g. cationic, anionic, or zwitterionic) chemical substances or synthetic polymers, or uncharged (e.g. cationic, anionic, or zwitterionic) chemical substances or synthetic polymers, or a combination thereof. Thus, in one aspect of a method or a kit of the invention, the flocculant comprises a cationic chemical substance, an anionic chemical substance, a zwitterionic chemical substance, a non-charged chemical substance or a combination thereof. In one aspect, the cationic, anionic, zwitterionic or non-charged substance comprises a quaternary ammonium or tertiary amine containing polymer. In one aspect, the flocculant is selected from the group consisting of ammonium acetate, magnesium chloride ($MgCl_2$), ferric chloride ($FeCl_3$), a salt of iron, a salt of aluminum, calcium chloride ($CaCl_2$), a polyacrylamide, aluminum ammonium sulfate, derivatives thereof, and a combination thereof.

In one aspect, a zwitterionic chemical substance comprises an amino acid (e.g., glycine, alanine; amino acids exist at zwitterions ("twin ions") at physiological pH), or any chemical (e.g., amino acid, small molecule or polymer) that would otherwise be nonionic at neutral pH (e.g. zwitterionic) but that will assume either a positive or negative charge at acidic or basic pH within the context of the invention. Zwitterions used in the methods and kits of the invention can be molecules that have ionizable groups that balance positive and negative charges at physiological pH. For example, both the amino group and the carboxyl group of each amino acid are ionizable, making them zwitterions. The carboxyl group (with a $pK_a$ of about 3) is deprotonated at physiological pH. The amino group is protonated at physiological pH. The $pK_a$ of ammonium ions is about 9.

In one aspect of the invention, the step at which the flocculation appears is critical in improving the efficiency of the flocculation process and the way it differs from the existing art of flocculation. Flocculation is generically used in numerous other applications and this invention incorporates the understanding that the stage at which the flocculant is added can be critical. Humic substances which are ubiquitous in aquatic and terrestrial environments play an important role in metal reduction by acting as electron shuttles. The quinine moieties in humic substances are thought to act as electron acceptors. It is through these mechanisms that humic acid reacts with select groups of inorganic salts of iron and aluminum and brings about the process of flocculation or metal-humic complex. Thus, in one aspect, the methods of the invention time the introduction of the flocculating agent at a stage in the protocol where the majority of the detergents, suspended solids and proteins, which are mostly ionic in nature are removed completely or reduced to an insignificant percentage. This sets the stage for removing the humic substances through flocculation, which are predominantly in a dissolved state and are believed to be a major component in the sample milieu apart from nucleic acid. The humic substances are available for selective flocculation to leave the nucleic acid in solution.

In one aspect, the flocculant used in the methods and compositions of the invention comprises a chemical substance such as a cationic chemical substance. In some embodiments, the flocculant is selected from the group consisting of ammonium acetate, magnesium chloride ($MgCl_2$), ferric chloride ($FeCl_3$), calcium chloride ($CaCl_2$), inorganic salts of iron and aluminum, a polyacrylamide (e.g., SUPERFLOC™, Cytec Industries), aluminum ammonium sulfate, derivatives thereof, and equivalents thereof (e.g., Braid et al., J. Microbiological Methods 52: 389-393 (2003)). In one aspect, a flocculant used in the methods and compositions of the invention comprises a cationic flocculant as disclosed, e.g., in U.S. Pat. Nos. 3,002,960; 3,316,181; 3,686,109; 3,692,673; 3,374,143; 4,010,131; 4,451,628; 4,565,635; 4,702,844; 4,693,830; 4,695,453; 4,147,681; 4,770,803; 5,552,316. In one aspect, a flocculant used in the methods and compositions of the invention comprises a cationic flocculant derived from alpha-beta unsaturated monomers.

Detergents or surfactants can be used to practice the methods or kits of the invention. In one aspect, the nucleic acid is contacted with the flocculant after separating a substantial amount of the detergent from the nucleic acid. In one aspect, a detergent is separated from the nucleic acid by contacting the nucleic acid and detergent with a detergent specific precipitant (e.g., ammonium acetate precipitates the detergent sodium dodecyl sulfate) and separating the precipitated detergent by centrifugation.

In one aspect, a substantial amount of the flocculant is separated from the nucleic acid; this can be done by any convenient procedure. For example, separation can be performed by contacting the flocculant and nucleic acid with a solid support under conditions in which the nucleic acid selectively binds to the solid support. In one aspect, the solid support comprises or consists of silica, and the nucleic acid adheres to the silica in the presence of a chaotropic substance (e.g., guanidinium chloride) and is eluted from the silica by removing the chaotrope and adding water. The term "substantial amount" as used herein (e.g., with regard to separating a detergent, a flocculant and/or a PCR inhibiting substance from a nucleic acid), in alternative embodiments, refers to the separated substance being present in a solution containing the nucleic acid after separation in an undetectable amount, or in an amount less than about 60%, less than about 50%, less than about 40%, less than about 30%, less than about 20%, less than about 10%, less than about 5%, less than about 1%, less than about 0.1%, less than about 0.01%, less than about 0.001%, less than about 0.0001%, less than about 0.00001%, less than about 0.000001% by weight of the separated substance to the weight of the nucleic acid.

In one aspect, the nucleic acid isolated by a method of the invention is utilized in a subsequent procedure, which can be performed after the nucleic acid is isolated (e.g., after the nucleic acid is separated from the flocculant) and in one aspect can be performed during the procedure of isolating the nucleic acid. For example, after a nucleic acid from one or more organisms in the soil sample is isolated, an oligonucleotide can be contacted with the nucleic acid. The oligonucleotide can be designed to hybridize to a particular nucleotide sequence potentially present in the nucleic acid. Nucleotide sequences for many organisms in soil samples are publicly available, e.g., NIH GenBank, and standard methods for designing and generating oligonucleotides are utilized to generate oligonucleotides that specifically hybridize to a nucleic acid of a particular organism, e.g., as described in Current Protocols In Molecular Biology (Ausubel, F. M., et al., eds. 2000) and Sambrook et al., "Molecular Cloning: A Laboratory Manual," 2nd ed. (1989). The oligonucleotides can be utilized in different types of procedures and analyses, including an amplification procedure (described hereafter). In one aspect, the invention provides a procedure in which multiple oligonucleotides are linked to a detectable label and contacted with the nucleic acid; the combination of oligonucleotides that hybridize to the nucleic acid is a signature for the type or types of organisms present in the sample.

In one aspect, the isolated nucleic acid or a portion thereof is amplified, where amplification can be performed using a polymerase chain reaction (PCR) procedure, reverse transcription, rolling circle replication and ligase-chain reaction. Using the kits and procedures described herein, the isolated nucleic acid can be substantially free of a substance that inhibits a PCR procedure (e.g., the isolated nucleic acid can be substantially free of a humic substance). PCR procedures are known (e.g., see U.S. Pat. Nos. 4,683,202; 4,683,195; 4,965,188; and 5,656,493) and generally, PCR processes are performed in cycles, where each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process that can be used in practicing the invention comprises treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products can be are stored for a time at a lower temperature (e.g., at 4° C.) and can be frozen (e.g., at −20° C.) before analysis.

Amplification products and DNA isolated from environmental and biological samples by the methods and kits of the invention can be detected by any suitable manner. For example, PCR amplification products in a sample can be resolved and detected by gel electrophoresis (e.g., plate or capillary gels composed of polyacrylamide or agarose), where bands corresponding to amplification products can be resolved by size and visualized by a light-emitting dye that intercalates with nucleic acid products in the gel (e.g., ethidium bromide). In one embodiment, PCR amplification products can be quantified by determining signal intensities of bands on a gel (e.g., by scanning the gel with a commercially available densitometer). In another embodiment, amplification products can be quantified by hybridization techniques (e.g., performing real time (RT)-PCR using commercially available TAQMAN® and LUX® products). In the latter embodiment, a double-labeled oligonucleotide complementary to a PCR product can be utilized in the quantification procedure, where one or both labels can be a fluorescent molecule (e.g., a carboxyfluorescein dye (FAM™ or FAMX™) at the 5' end of the oligonucleotide and a carboxytetramethylrhodamine dye (TAMRA™) at the 3' end of the oligonucleotide (e.g., these and other fluorescent dyes are commercially available, e.g., SYNTHEGEN, LLC, Houston, Tex.). Lower limits of the PCR detection process can be determined by serially diluting a sample and determining the lowest detectable amount of organism nucleic acid in the soil sample.

In some embodiments, an isolated nucleic acid is RNA, and in one aspect, the RNA is reverse transcribed, such that complementary DNA (cDNA) is generated. Methods and products for reverse transcribing RNA are known (e.g., SUPERSCRIPT™ II Reverse Transcriptase, Invitrogen, San Diego, Calif.). The cDNA in one aspect can be quantified, such as by using a method described above, and in one aspect the cDNA is quantified after the cDNA produced by the reverse transcription procedure is amplified.

In one aspect, the isolated nucleic acid is contacted with a restriction enzyme. In such embodiments, comparative restriction digests can be assessed to determine whether a restriction digest pattern signature for a particular organism or organisms is present in the soil sample. In other embodiments, the isolated nucleic acid is analyzed by mass spectrometry. Mass spectrometry procedures are known (e.g., U.S. Pat. Nos. 5,547,835; 5,605,798; 5,691,141; 5,849,542; 5,869,242; 5,928,906; 6,043,031; and 6,194,144) and can be performed after a region of the isolated nucleic acid is amplified, and can be utilized to detect polymorphic variants in the isolated nucleic acid. In some embodiments, the isolated nucleic acid is immobilized to a solid surface. Examples of solid surfaces include but are not limited to a glass slide or plate, a silicon wafer or chip, a well of a microtiter plate (e.g., 96-well or 384-well plate), and a plastic surface of a vessel suitable for growing cells.

The invention provides kits for isolating a nucleic acid from a sample, e.g., an environmental or biological sample, which comprises a flocculant and instructions describing a method for use according to any of the methods of the invention for isolating the nucleic acid from the soil sample. The kit in one aspect further comprises a detergent, which can be utilized in a process for extracting nucleic acids from the soil. In some embodiments, the kit comprises homogenizing methods and compositions, including beads (e.g., glass beads or garnet beads), and in one aspect includes an adaptor for connecting tubes containing the sample to a vortex apparatus (e.g., Vortex Adapter, Mo Bio Laboratories, Carlsbad, Calif.). The kit in one aspect includes a solid support useful for separating a flocculant from a nucleic acid, such as a silica medium, where the solid support in one aspect can be in an apparatus adapted to fit into a tube for use in centrifugation. In one aspect the kit comprises a chaotropic substance (e.g., guanidinium chloride), often used in a process for separating a flocculant from a nucleic acid. In one aspect the kit comprises a solution useful for precipitating a detergent. In one aspect, the kit comprises one or more solutions useful for performing the method of use included in the instructions. In one aspect, the kit comprises one or more tube vessels useful for performing the method of use. Where tube vessels are included in the kit, the vessels can be sterile. In some embodiments, the kit includes components useful for further processing the isolated nucleic acid. For example, in one aspect, the kit includes one or more components selected from the group consisting of one or more oligonucleotides, free nucleotides and a polymerase capable of amplifying all or part of an isolated nucleic acid. In one aspect, the kit includes one or more oligonucleotides that hybridize to a bacterial nucleic acid, e.g., a *Bacillus anthracis*, or other agent associated with bioterrorism that contain DNA or RNA.

Alternative embodiments comprise procedures and kits for purifying a nucleic acid already extracted from a sample, e.g., environmental or biological samples. Such procedures and kits are applicable to a nucleic acid extracted from environmental or biological samples using a kit or procedure different than one of this invention. Thus, these procedures and kits of the invention are useful for purifying contaminated nucleic acid preparations isolated from a sample, e.g., environmental or biological samples, such as soil samples (e.g., separating substances from the nucleic acid that inhibit downstream procedures). The purification procedures and kits can be useful for separating contaminants from the extracted nucleic acids, such as contaminant substances that inhibit PCR and/or hybridization of an oligonucleotide to the nucleic acid (e.g., a humic substance). The purification procedures are applicable to a variety of nucleic acid preparations, including those that do not yield detectable amplification products after performing PCR, and those that can be colored (e.g., nucleic acid preparations that are yellow to brown in color). Thus, provided herein is a method for purifying a contaminated nucleic acid extracted from a sample, e.g., environmental or biological samples, such as soil samples comprising contacting the nucleic acid with a flocculant.

In one aspect, the flocculant is separated from the nucleic acid in a subsequent step, as described above. The nucleic acid in one aspect can be contacted with a detergent, and a substantial amount of the detergent can be separated from the nucleic acid before the nucleic acid is contacted with the flocculant. As described above, a substantial amount of the detergent in one aspect can be separated from the nucleic acid by contacting the detergent with a substance that selectively precipitates the detergent and then subjecting the mixture to centrifugation, which pellets the precipitated detergent and leaves the nucleic acid in the supernatant fraction.

The invention provides DNA and RNA targeting techniques that allow in situ analysis of microbial communities in soil environments. While DNA based studies provide community structure information and phylogenetic relationships among the various groups, total RNA isolation using the methods and kits of the invention can make it possible to study mRNA expression levels that provide valuable information on functional activities of specific microbial genes within microbial populations in soil. Because the methods and kits of the invention can make it possible to identify, isolate and/or amplify total cell nucleic acid, mitochondrial, nuclear, chloroplast or other organelle nucleic acid, including RNA and DNA, can also be identified, isolated and/or amplified using the methods and kits of the invention. In order to study gene expression in soil, the invention provides a robust protocol for extraction of total, nondegraded RNA. The invention provides a reliable recovery process for messenger RNA (mRNA) from differing natural environments with microbial heterogeneity, variations in experimental conditions, differences in the interactions of DNA and RNA molecules with environmental sample matrices, adsorption characteristics of clay fractions to nucleic acids and the labile nature of RNA to nucleases and oxidation-reduction processes that occur naturally in soils and other natural environments.

In one aspect, the invention provides a distinct departure from the traditional method of adding the flocculating reagent and detergent before sample lysis to provide a method whereby high organic content samples produce nucleic acid from contaminating substances. The invention provides for the use of flocculating materials for purifying nucleic acid from environmental and biological samples by addition of a flocculating material to a nucleic acid (and contaminant) containing sample following partial purification of the nucleic acid from the starting environmental and biological sample and its components (e.g. soil, cellular debris, humic substances and detergent). For example, in one aspect, the invention provides a method for purifying a contaminated nucleic acid extracted from an environmental soil sample, which comprises contacting the nucleic acid with a flocculant. In one aspect, the flocculant is separated from the nucleic acid in a subsequent step as described above with the use of silica membranes. The nucleic acid purification process may include contact with a detergent, and in one embodiment, a substantial amount of the detergent is separated from the nucleic acid before the nucleic acid is contacted with the flocculant. In one aspect, a substantial amount of the detergent is separated from the nucleic acid by contacting the detergent with a substance that selectively precipitates the detergent. In one aspect, the precipitate is removed by passive settling or by subjecting the mixture to centrifugation, which pellets the precipitated detergent and leaves the nucleic acid in the supernatant fraction.

The process described herein is not dependent upon, but may include the use of a component for facilitating sample disruption and nucleic acid liberation prior to or contemporaneous to flocculent addition to the sample (e.g., homogenizing beads). It should be noted that the use of a flocculating agent with a sample that does not contain contaminating substances will not affect the nucleic acid purity or use in downstream applications.

The invention provides kits for separating nucleic acids either extracted directly from an environmental or biological sample, or for DNA previously purified by non-flocculating methods from samples containing contaminating substances that inhibit downstream nucleic acid application. The purification procedures and kits of the invention are applicable to a variety of nucleic acid preparations, including those that do not yield detectable amplification products after performing PCR and those whose refractive index indicate clear to colored (e.g., nucleic acid preparations that are yellow to brown in color) composition. The kits and methods of the invention are adaptable to a wide range of sample volume, mass and type and nucleic acid yield.

The invention will be further described with reference to the following examples; however, it is to be understood that the invention is not limited to such examples.

EXAMPLES

Example 1

DNA Isolation from up to 250 Milligram of Environmental Sample

The following example describes an exemplary purification process of the invention. Nucleic acid from several different soil types was isolated and examined using the method describe herein. The kit and method were tested on soils, sediments, composts and manure representing a broad range of organic carbon and nitrogen content and varying sand/silt/clay compositions. The same kit was also tested and found to be effective in isolating DNA free of contaminants from plant tissues such as leaves, roots, stems and seed materials Specifically, for soils, there were nine samples, which included landfill 0-3 inches deep; landfill 3-6 inches deep; late-stage compost; coffee compost; marine sediment; lake sediment; mud sediment; horse manure and mulch-top soil. DNA was extracted from these samples using the method described herein and analyzed by agarose gel electrophoresis to determine DNA quality by visually identifying a discreet DNA band greater than 23,000 molecular weight (23 kbp). The presence of shorter DNA fragments is an indication of DNA breakage, or shearing, during the process. The usefulness of the purified DNA to downstream applications, in part determined by whether the sample is substantially free from PCR-inhibiting substances, was assessed by PCR amplification using consensus primers specific for a 520 base pair (bp) region of eubacterial 16S ribosomal DNA.

The example below uses a vortex mechanical lysis process extraction/homogenization procedure (Vortex Adapter, Mo Bio Laboratories, Carlsbad, Calif.) and is incorporated to illustrate its use. The procedure has been shown to work without mechanical lysis with reduced nucleic acid yield. The result is that the described procedure produces PCR quality DNA with minimal shearing in approximately 45 minutes. The purified DNA was directly amplified by PCR in all samples tested. No dilution steps, PCR optimization or further DNA purification was necessary for performing PCR using the DNA isolated from soil.

Procedure for Isolating DNA from 0.25 Grams of Environmental Sample

1. Add 0.25 grams of sample to a soil bead tube containing 750 microliters (μl) bead solution.
2. Vortex the samples and add 60 μl of C1.
3. Place the tubes on a Vortex Adapter (Mo Bio Laboratories, Carlsbad, Calif.) and vortex the tubes on the highest setting for 10 minutes.
4. Centrifuge the tube at 10,000×g for 30 seconds at room temperature and transfer the supernatant to a new tube.
5. Add 250 μl of C2 and vortex to mix. Incubate the sample at 4° C. for 10 minutes and then centrifuge the tube at 10,000×g for 1 minute at room temperature. Transfer the supernatant to a new tube.
6. Add 200 μl of C3 and incubate the sample at 4° C. for 10 minutes.
7. Centrifuge the tube at 10,000×g for 10 minutes at room temperature. Transfer the supernatant to a new tube.
8. Add 1200 μl of C4 and mix by inversion.
9. Load the samples onto the spin column. Centrifuge the column at 10,000×g for 30 seconds at room temperature.
10. Add 500 μl of solution C5 to the spin column and centrifuge at 10,000×g for 30 seconds at room temperature.
11. Decant the flow-through and recentrifuge the filter at 10,000×g for 30 seconds at room temperature.
12. Transfer the spin basket to a new tube and elute DNA with 100 μl of solution C6 by centrifuging at 10,000×g at room temperature.

Results

See FIG. 1: DNA purified by the method described herein was characterized by agarose gel electrophoresis. FIG. 1: Total genomic DNA isolated from 0.25 grams of representative soil types. DNA was analyzed by 0.8% TAE agarose gel electrophoresis, ethidium stained and photographed. Samples were obtained from landfill (0-3 inches deep, lane 1), landfill (3-6 inches deep, lane 2), late stage compost (lane 3), coffee compost (lane 4), marine sediment (lane 5), lake sediment (lane 6), mud sediment (lane 7), horse manure (lane 8) mulch topsoil (lane 9). M=DNA molecular size marker.

Figure 2:
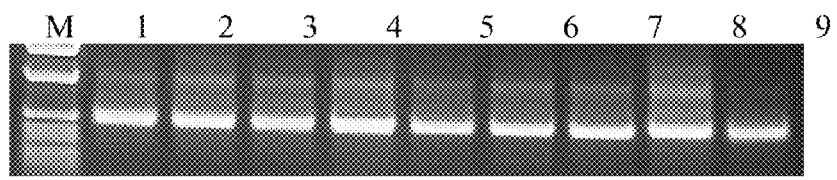
FIG. 2 illustrates an agarose gel electrophoresis showing PCR amplified total genomic DNA isolated in FIG. 1, as described in Example 1, below.

Using the procedure disclosed above, genomic DNA was isolated from all tested soil samples. PCR amplification of the isolated genomic DNA from FIG. 2 using primers to eubacterial DNA indicated that PCR products were produced from each soil sample, indicating the nucleic isolation procedure described herein had successfully purified eubacterial genomic DNA. FIG. 2 illustrates an agarose gel electrophoresis showing PCR amplified total genomic DNA isolated in FIG. 1, where the purified eubacterial genomic DNA was PCR amplified using primers to eubacterial DNA. M=DNA molecular size marker.

Figure 3:
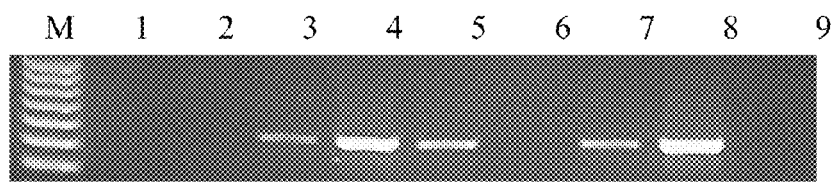
FIG. 3 illustrates an agarose gel electrophoresis showing a comparison of PCR amplification of eubacterial DNA isolated using a commercially available kit representative of the existing art, as described in Example 1, below.

DNA was isolated from the soil types used in FIG. 1, using the ULTRACLEAN™ Soil DNA Kit (Mo Bio Laboratories, Carlsbad, Calif.) FIG. 3 shows PCR amplification of the genomic DNA using primers to eubacterial DNA. M=DNA molecular size marker. Note that DNA isolated with the ULTRACELAN™ Soil DNA Kit contained contaminants removed using the invention that prevented PCR amplification in 4 of the 9 tested samples.

Reagents

| | |
|---|---|
| Bead Tube | Bead tubes with garnet beads and 750 μl 181 mM NaPO$_4$, 121 mM guanidinium isothiocyanate |
| C1 | 150 mM NaCl, 4% SDS, 0.5 M Tris |
| C2 | 133 mM Ammonium acetate |
| C3 | 120 mM aluminum ammonium sulfate dodecahydrate |
| C4 | 5 M GuHCL, 30 mM Tris, 9% isopropanol |
| C5 | 10 mM Tris, 100 mM NaCl, 50% EtOH |
| C6 | 10 mM Tris |

The reagents and method for purifying nucleic acid from environmental and biological samples will have broader application if the process is scaleable in the amount of sample processed and the ability to successfully use it in downstream applications. Example 2 provides evidence of the invention scalability.

Example 2

Purification of DNA Extracted from up to 10 Grams of Soil

The following example describes an exemplary purification process of the invention.

1. Add up to 10 grams of sample to a soil bead tube containing 15 ml bead solution.
2. Briefly vortex the samples and add 1.2 ml of C1.
3. Place the tubes on a vortex adapter (Mo Bio Laboratories, California) and vortex the tubes on the highest setting for 10 minutes.

4. Centrifuge the tube at 2,500×g for 30 seconds at room temperature and transfer the supernatant to a new tube.
5. Add 5 ml of C2 and vortex to mix. Incubate the sample at 4° C. for 10 minutes and then centrifuge the tube at 2,500×g for 4 minutes at room temperature. Transfer the supernatant to a new tube.
6. Add 4 ml of C3, invert to mix and incubate at 4° C. for 10 minutes.
7. Centrifuge the tube at 2,500×g for 4 minutes at room temperature. Transfer the supernatant to a new tube.
8. Add 30 ml of C4 to each tube and mix by inversion.
9. Load the samples onto the spin column. Centrifuge at 2,500×g for 30 seconds at room temperature. Repeat steps 8 and 9 twice
10. Add 10 ml of solution C5 to the column and centrifuge at 2,500×g for 5 minutes at room temperature.
11. Transfer the spin basket to a new tube and elute the nucleic acid with 5 ml of solution C6 by centrifuging at 2,500×g at room temperature.

Figure 4:
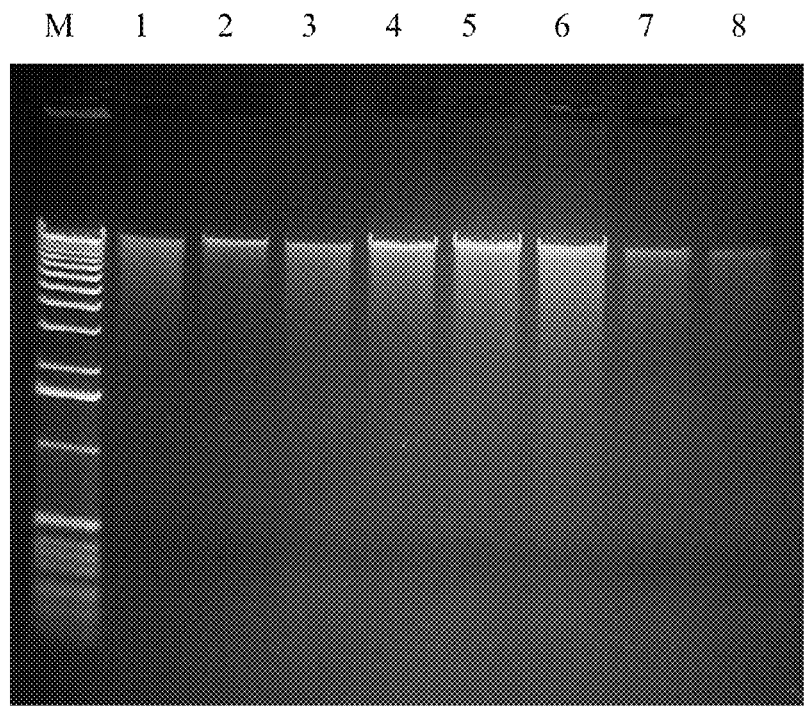
FIG. 4 illustrates an agarose gel electrophoresis showing total genomic DNA was isolated from different soil samples, as described in Example 2, below.
Figure 5:
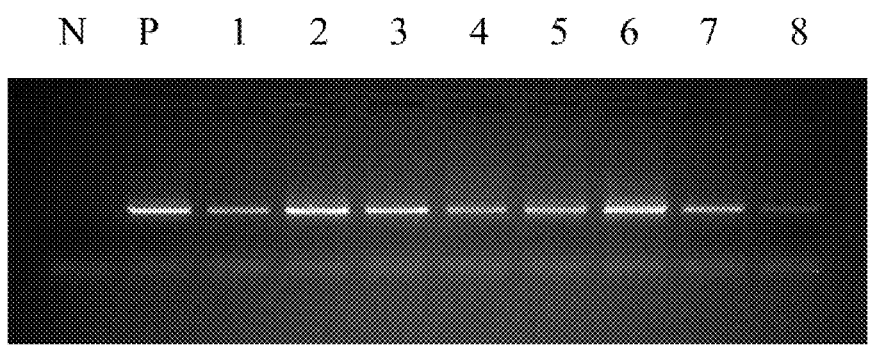
FIG. 5 illustrates an agarose gel electrophoresis showing total genomic DNA PCR amplified using primers to the *Bacillus* spp., as described in Example 2 and 3, below.
Figure 6:
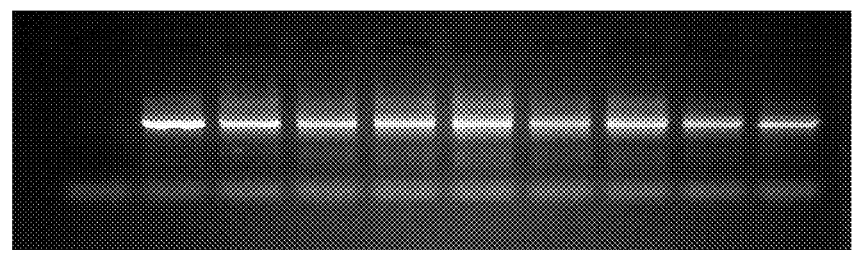
FIG. 6 illustrates an agarose gel electrophoresis showing total genomic DNA PCR amplified using primers to the *Streptomyces* spp., as described in Examples 2 and 3, below.

See FIGS. 4, 5 and 6, which indicate that the process described herein is capable of isolating DNA from different types of environmental samples (FIG. 4) and is capable of purifying endogenous soil organism DNA in a scaleable process. Importantly, the Example provides evidence the process isolates DNA free of PCR inhibiting substances (FIGS. 5 and 6).

FIG. 4: Total genomic DNA was isolated from up to 10 grams of 8 different soil samples using the methods described herein. DNA analyzed on 1 % TAE agarose gel and ethidium stained. M=Marker DNA. Soil types are identified below.

FIG. 5: Total genomic DNA isolated in FIG. 3 using methods described herein was PCR amplified using primers to the *Bacillus* spp. Amplified DNA was analyzed on 0.8% TAE agarose and ethidium stained. N=Negative control lacking template. P=Positive control template. Soil types and amount are identified below.

FIG. 6: Total genomic DNA isolated from soil samples identified in FIG. 3 using the methods described herein was PCR amplified using primers to the *Streptomyces* spp. DNA was analyzed on 1 % TAE agarose and ethidium stained. N=Negative control lacking template. P=Positive control template. Soil types and amount are identified below.

| Sample Lane | Type | Amount processed (grams) |
| --- | --- | --- |
| 1 | Iowa corn field | 10 |
| 2 | California strawberry field | 10 |
| 3 | Cardiff lagoon sediment | 10 |
| 4 | Carlsbad lagoon sediment | 10 |
| 5 | Home compost | 5 |
| 6 | San Diego City compost | 5 |
| 7 | Commercial potting mixture | 2.5 |
| 8 | Commercial peat moss | 2.5 |

Example 3

Procedure for Removing Contaminants from Nucleic Acid

Figure 7:
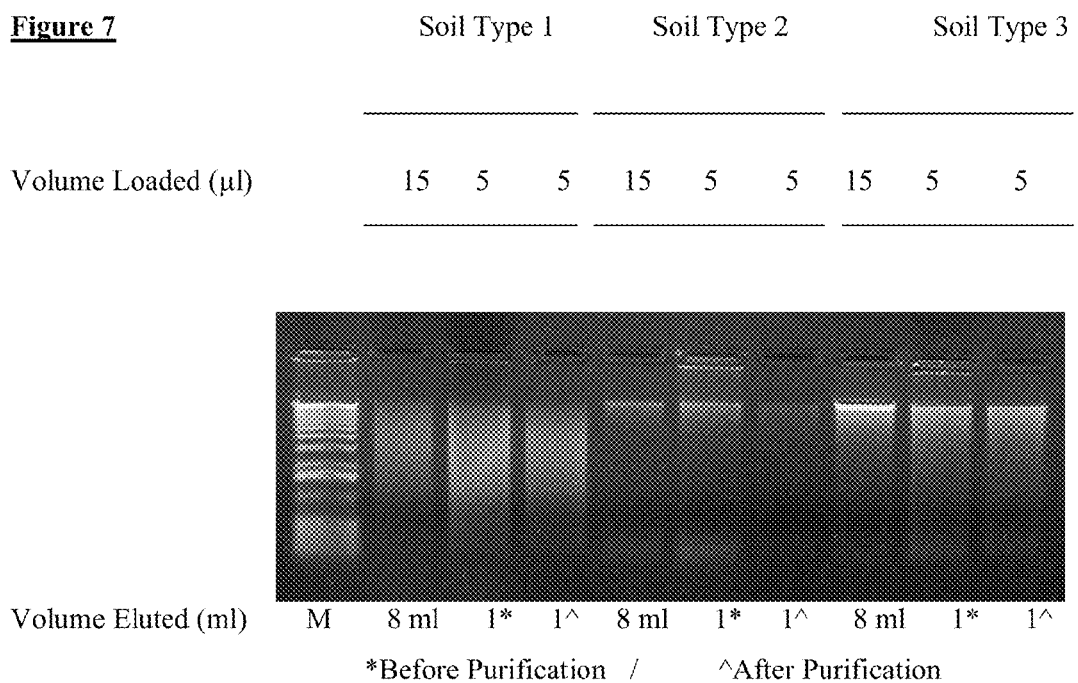
FIGS. 7 and 8 illustrates agarose gel electrophoreses showing nucleic acid isolated from soil samples (see Table 1, Example 3) and tested by PCR, as described in Example 3, below.
Figure 8:
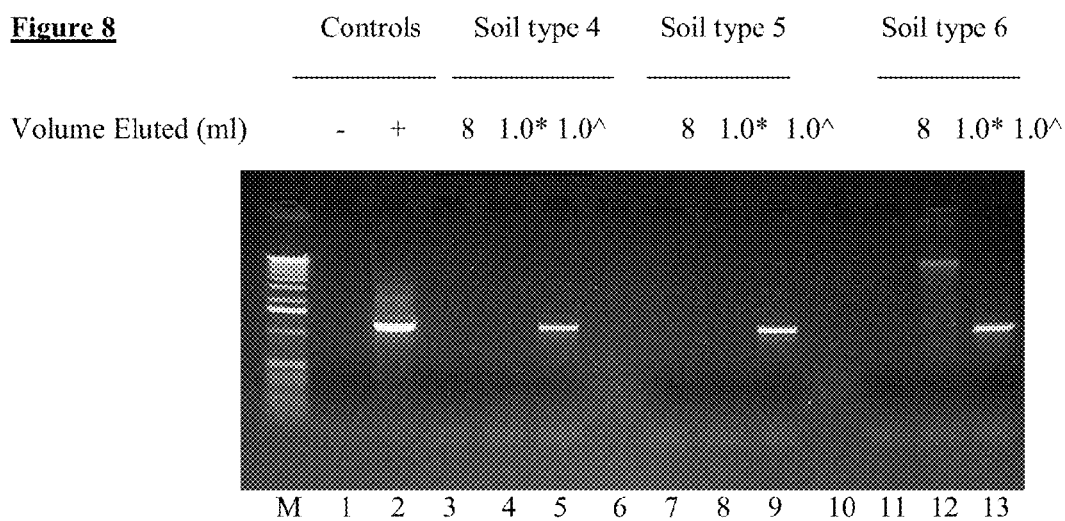

The following exemplary purification process of the invention produces nucleic acid that may be used in downstream processes from previously purified nucleic acid that has contaminating substances that have prevented use of the nucleic acid in a downstream application (e.g. PCR). The nucleic acid was isolated using the ULTRACLEAN MEGASOIL DNA ISOLATION KIT and processed using the procedure and reagents indicated below and analyzed (FIG. 7,). The nucleic acid was tested in PCR (FIG. 8).

Nucleic acid was purified from 3 different environmental samples (identified by 8 ml). The nucleic acid was analyzed by 0.8% TAE agarose gel electrophoresis and ethidium stained for detection. The soil types are identified below. The DNA was concentrated to a volume of 1 ml using isopropanol precipitation and is presented in the lanes labeled 1*. The nucleic acid in 1* was processed with the contamination removal protocol and reagents described herein and analyzed in the lanes labeled 1^. The nucleic acid in FIG. 7 appears equivalent for each sample set following isopropanol precipitation and contaminant removal.

FIG. 7 shows the use of the nucleic acid in FIG. 6 in a PCR procedure. For each sample, the lanes labeled 8 ml and 1* show PCR inhibition and input nucleic acid is unable to produce an amplification product. The lanes labeled 1^, which have been processed with the contaminant removal process described herein, show successful removal of the contaminant and PCR amplification product.

1. Add up to 1000 µl of DNA sample to a clean tube.
2. Add 460 µl of bead solution per 150 µl of DNA. Invert to mix.
3. Add 140 µl of C1 and invert to mix.
4. Add 560 µl of C2 and invert to mix. Incubate the sample at 4° C. for 5 minutes and centrifuge the sample at 10,000×g for 1 minute at room temperature.
5. Transfer the supernatant to a clean tube.
6. Add 460 µl of C4 and invert to mix. Incubate the sample at 4° C. for 10 minutes.
7. Centrifuge the sample at 10,000×g for 10 minutes at room temperature.
8. Transfer the supernatant into a clean tube.
9. Add 2750 µl of C5 and vortex to mix.
10. Load the sample onto a spin column and centrifuge at 2,500×g for 1 minute at room temperature.
11. Add 2000 µl C6 to the column and centrifuge at 2,500×g for 3 minutes at room temperature.
12. Decant the flow-through and centrifuge the column at 2,500×g for 5 minutes at room temperature.
13. Transfer the spin basket to a new tube and add 1000 µl of solution C7 to elute the DNA. Centrifuge at 2,500×g for 2 minutes at room temperature.

Kit Reagents

| | |
| --- | --- |
| Bead solution | 181 mM NaPO$_4$, 121 mM GITC |
| C1 | 150 mM NaCl, 4% SDS, 0.5 M Tris |
| C2 | 133 mM Ammonium acetate |
| C3 | 120 mM aluminum ammonium sulfate dodecahydrate |
| C4 | 5 M GuHCL, 30 mM Tris 9% isopropanol |
| C5 | 10 mM Tris, 100 mM NaCl, 50% EtOH |
| C6 | 10 mM Tris |

In FIG. 8, the nucleic acid from FIG. 7 was used in a PCR reaction. The lanes labeled (−) and (+) are negative and positive control reactions. The PCR amplified DNA was analyzed by electrophoresis on 0.8% TAE agarose followed by ethidium bromide staining. In FIG. 8: *Before Purification, ^After Purification and removal of contaminating substances using methods described herein.

Soil Type and Amount Processed
Soil Type 1. Compost (18-21" deep) (5 g)
Soil Type 2. Home Compost (5 g)
Soil Type 3. Compost-SD (5 g)

RNA isolated from 8 different soil types, as noted in Table 2, below, and run on a 1%, 1× TAE gel for 45 minutes at 100 v., see FIG. 9.

TABLE 2

List of soil samples used to isolate RNA

| Sample Lane | Type | Amount processed (grams) |
|---|---|---|
| 1 | Lawn soil | 2 |
| 2 | California strawberry field | 2 |
| 3 | Rhizosphere soil | 2 |
| 4 | Cardiff lagoon sediment | 2 |
| 5 | RCP amended soil | 2 |
| 6 | San Diego City compost | 1 |
| 7 | Iowa Corn field | 2 |
| 8 | East San Diego County soil (sandy) | 2 |

Example 4

RNA Isolation from up to 2.0 Grams of Environmental Sample

The following example describes an exemplary purification process of the invention. RNA was isolated from several different soil types and examined using a method and described herein. The kit and method were tested on soils, sediments, composts and manure representing a broad range of organic carbon and nitrogen content and varying sand/silt/clay composition. Specifically, there were eight samples, which included a heavily fertilized lawn soil, soil from a straw berry cultivated field in Southern California, a sediment fed by sea water, a commercially amended soil, city compost, soil from a corn field in Iowa, soil from rhizosphere region of a plant, and a sandy soil from east of San Diego County. RNA was extracted from these samples using the method described herein and analyzed by agarose gel electrophoresis to determine RNA quality by visually identifying a discreet 23S band and a 16S band. The usefulness of the purified and digested RNA to downstream applications, in part determined by whether the sample is substantially free from PCR-inhibiting substances, was assessed by RT-PCR amplification using consensus primers specific for a 600 base pair (bp) region of bacteria belonging to *Bacilli* group and a 1.2 kb base pair region of *Streptomycetes* group.

The example below uses a vortex mechanical lysis process extraction/homogenization procedure and is incorporated to illustrate its use. The result is that the described procedure produces RT-PCR quality RNA which are intact from all the soils tested in this study, in approximately 2.5 hours. The purified RNA, after digestion with DNase enzyme and subsequent purification, was directly amplified by RT-PCR in all samples tested. No dilution steps, RT-PCR optimization or further RNA purification was necessary for performing RT-PCR using the RNA isolated from soil.

Procedure for Isolating RNA From 2.0 Grams of Environmental Sample

1. Add 2 grams of sample to a soil bead tube containing 1.5 of silica carbide beads.
2. Add 2.5 ml of Solution SR1, vortex to mix and then add 250 µl of Solution SR2, vortex to mix.
3. Add 800 µl of Solution SR3 and vortex to mix.
4. Place the tubes on a vortex adapter (Mo Bio Laboratories, California) and vortex the tubes on the highest setting for 5 minutes.
5. Add 3.5 ml of SR 4 (Phenol:Chloroform:Isoamylalcohol [50:49:1)] {pH 4.5 to 8.0}) and continue bead beating the tubes for 10 minutes.
6. Centrifuge the tube at 2500×g for 10 minutes at room temperature and transfer the aqueous phase to a new 15 ml tube.
7. Add 1.5 ml of Solution SR5 and vortex to mix. Incubate the sample at 4° C. for 10 minutes and then centrifuge the tube at 2500×g for 10 minute at room temperature. Transfer the supernatant to a new tube.
8. Add 5 ml of Solution SR6 (100% isopropanol) and incubate the sample at −20° C. for 30 minutes.
9. Centrifuge the tube at 2500×g for 30 minutes at room temperature. Discard the supernatant and air-dry the pellets for 5 minutes at room temperature.
10. Resuspend the pellet in 1 ml of Solution SR7 and load it onto a pre-equilibrated RNA capture column (pre-equilibrated with 2 ml of SR7. Discard the flow-through.
11. Wash the columns with 1 ml of SR7 and discard the flow-through.
12. Elute the columns with 1 ml of Solution SR8.
13. Transfer the eluted SR8 to a 2 ml tube and add an equal of 100% isopropanol. Incubate at −20° C. for 10 minutes followed by centrifuging the tubes at 16,000×g for 15 minutes.
14. Discard the flow-through and air-dry the pellet.
15. Resuspend the pellet in 100 µl of Solution SR9.

Results

Figure 9:
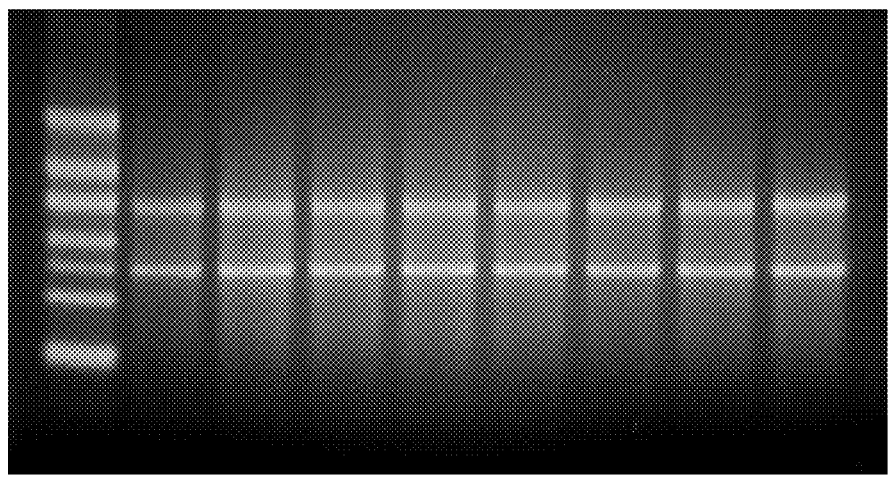
FIG. 9 illustrates an agarose gel electrophoresis showing RNA isolated from 8 different soil types, as noted in Table 2, Example 3, as described in Example 3, below below.

See FIG. 9. RNA purified by the method described herein was characterized by agarose gel electrophoresis. Using the procedure disclosed above, RNA was isolated from all tested soil samples. RT-PCR amplification of the isolated RNA from FIG. 9 using two different primer sets (one for *Bacilli* group and the other for *Streptomycetes* group) indicated that RT-PCR products were produced from each soil sample, indicating the RNA isolation procedure described herein had successfully purified RNA.

Reagents

| Bead Tube | Bead tubes with 1.5 g of silica carbide in a 15 ml screw cap tube. |
|---|---|
| PowerSoil ™ RNA BeadSolution | 181 mM NaPO4, 121 mM guanidinium thiocyanate |
| SR1 | 150 mM NaCl, 4% SDS, 0.5 M Tris |
| SR2 | 120 mM aluminum ammonium sulfate dodecahydrate |
| SR3 | 5 M NaCl in 22 mM citric acid anhydrous salt, 29 mM trisodium citrate, dehydrate, pH 5.0–5.2 Phenol:Chloroform:Isoamyl alcohol (50:49:1) |
| SR4 | 100% Isopropanol |
| SR5 | 500 mM NaCl in 50 mM 2-(N-morpholino)propane-sulfonic acid (MOPS) with 15% isopropanol, pH 7.0 |
| SR6 | 750 mM NaCl in 50 mM MOPS with 15% isopropanol, pH 7.0 |
| SR7 | DEPC-treated water |

Figure 10:
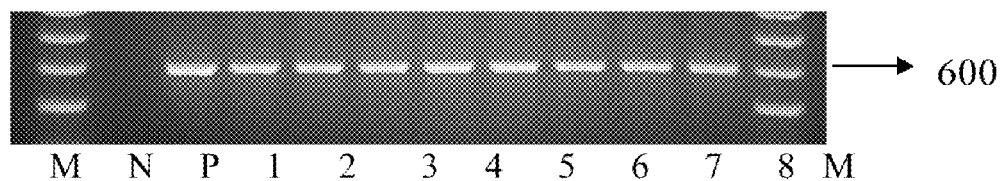
FIGS. 10 and 11 illustrate agarose gel electrophoreses showing RT-PCR amplification of total RNA from a soil sample with a primer set specific for microorganisms belonging to *Bacilli* group and *Streptomycetes* group, respectively.

As illustrated in FIG. 10, total RNA isolated was digested with RNase-free DNase and then purified by phenol:chloroform extraction followed by isopropanol precipitation. The DNA-free RNA was used undiluted in a RT-PCR reaction with a primer set specific for a 1200 bp fragment of microorganisms belonging to *Streptomycetes* group. M—Marker, N—Negative control, P—Positive control and samples 1 through 8 as presented in the Table 2.

Figure 11:
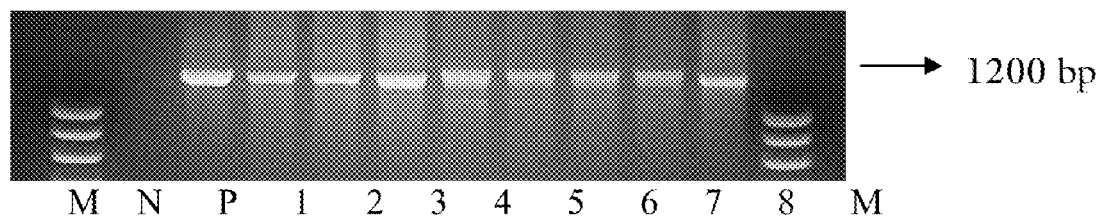

As illustrated in FIG. 11, total RNA isolated was digested with RNase-free DNase and then purified by phenol:chloroform extraction followed by isopropanol precipitation. The DNA-free RNA was used undiluted (1 l/50 μl) in a RT-PCR reaction with a primer set specific for a 1200 bp fragment of microorganisms belonging to Streptomycetes group. M—Marker, N—Negative control, P—Positive control and samples 1 through 8 as presented in the Table 2.

Modifications may be made to the foregoing without departing from the basic aspects of the invention. Although the invention has been described in substantial detail with reference to one or more specific embodiments, those of skill in the art will recognize that changes may be made to the embodiments specifically disclosed in this application, yet these modifications and improvements are within the scope and spirit of the invention.

All documents, including patents, patent application and publications cited herein, including all documents cited therein, tables, and drawings, are hereby expressly incorporated by reference in their entirety for all purposes.

While the invention has been described in detail with reference to certain Exemplary aspects thereof, it will be understood that modifications and variations are within the spirit and scope of that which is described and claimed.

What is claimed is:

1. A method for removing a contaminant or inhibitor from a nucleic acid-comprising sample, wherein the contaminant or inhibitor inhibits the amplification or hybridization of the nucleic acid in the sample, or inhibits an enzymatic reaction utilizing the nucleic acid in the sample, the method comprising the steps of:
   (a) providing a reaction mixture comprising the sample, a chaotropic agent, ammonium acetate or an equivalent, and a detergent;
   (b) isolating the nucleic acid and remaining contaminants and inhibitors from the reaction mixture in a supernatant; and
   (c) contacting the nucleic acid supernatant with a flocculant resulting in the further removal of the contaminant or the inhibitor from the supernatant.

2. The method of claim 1, wherein the contaminant or inhibitor is selected from the group consisting of a polyphenol, a polysaccharide, a humic substance, an enzymatic inhibitor from soil, a humic polymer, an organic compound from compost, a decomposing plant material, a plant pigment, a plant cell wall, a chitin, a photosynthetic pigment, a humic acid, a fulvic acid, a phenolic polymer and/or phenolic oligomer, a tannin, a humin, and a phenolic.

3. The method of claim 1, wherein the equivalent is sodium chloride, ammonium sulfate, potassium acetate, or sodium acetate.

4. The method of claim 1, wherein the flocculant is aluminum ammonium sulfate, ammonium sulfate dodecahydrate; aluminum ammonium sulfate dodecahydrate; aluminum potassium sulfate, aluminum chlorohydrate, aluminum sulfate, calcium oxide, iron (III) chloride, iron (II) sulfate, sodium aluminate, or sodium silicate.

5. The method of claim 1, wherein the sample comprises an environmental or a biological sample, and optionally the environmental or biological sample comprises a sample derived from an animal, animal remains, a food, a microorganism, a plant or its components, soil, sediment, rock, reef, sludge, compost, decomposing biological matter, a biopsy, a histological sample, a semen sample, a blood or saliva sample, any body fluid sample, a hair sample, a skin sample, a fecal sample, archaeological remains, a peat bog, compost, oil, water, terrestrial water or subterranean water, atmospheric and industrial water, dust, urban dust, commercial potting mixtures or soil amendments, deep sea vents, or air.

6. The method of claim 1, wherein the nucleic acid comprises an RNA (mRNA, tRNA, rRNA, iRNA) or a DNA or a combination thereof.

7. The method of claim 1, wherein the detergent is selected from the group consisting of sodium dodecyl sulfate (SDS), sarkosyl, sodium lauryl sarcosinate, cetyltrimethyl ammonium bromide (CTAB), cholic acid, deoxycholic acid, benzamidotaurocholate (BATC), octyl phenol polyethoxylate, polyoxyethylene sorbitan monolaurate, tert-octylphenoxy poly(oxyethylene)ethanol, 1,4-piperazinebis-(ethanesulfonic acid), N-(2-acetamido)-2-aminoethanesulfonic acid, polyethylene glycoltert-octylphenyl ether (Triton®X-100), (1,1,3,3-tetramethylbutyl)phenyl-polyethylene glycol (Triton®X-114), and a combination thereof.

8. The method of claim 1, further comprising:
   (d) purifying or isolating the nucleic acid; and/or
   (e) detecting or characterizing the nucleic acid, wherein the detecting or characterizing results in the determination that the nucleic acid is from an organism that produces a spore or a toxin.

9. The method of claim 8, wherein the toxin is a bacterial toxin.

10. The method of claim 1, further comprising:
    (d) purifying or isolating the nucleic acid; and/or
    (e) detecting or characterizing the nucleic acid, wherein the detecting or characterizing results in the determination that the nucleic acid is from an organism that produces a biohazard agent.

11. The method of claim 10, wherein the biohazard agent is a bacterial toxin.

12. The method of claim 1, further comprising purifying or isolating the nucleic acid after step (c).

13. The method of claim 1, wherein the sample is an unprocessed, preserved, freshly isolated, crude or unrefined sample.

14. The method of claim 1, wherein the reaction mixture of step (a) is mixed or vortexed.

15. The method of claim 1, wherein the isolating in step (b) comprises centrifuging the reaction mixture and harvesting a nucleic acid-comprising supernatant.

16. The method of claim 1, further comprising after step (c), detecting or characterizing the nucleic acid.

17. A method for removing a contaminant or inhibitor from a nucleic acid-comprising sample, wherein the contaminant or inhibitor inhibits the amplification or hybridization of the nucleic acid in the sample, or inhibits an enzymatic reaction utilizing the nucleic acid in the sample, the method comprising the steps of:
    (a) providing a reaction mixture comprising the sample, a chaotropic agent, ammonium acetate, and a detergent;
    (b) isolating the nucleic acid and remaining contaminants and inhibitors from the reaction mixture in a supernatant; and
    (c) contacting the nucleic acid supernatant with aluminum ammonium sulfate resulting in the further removal of the contaminant or the inhibitor from the supernatant.

18. The method of claim 17, further comprising purifying or isolating the nucleic acid after step (c).

19. The method of claim 17, wherein the sample is an unprocessed, preserved, freshly isolated, crude or unrefined sample.

20. The method of claim 17, wherein the reaction mixture of step (a) is mixed or vortexed.

21. The method of claim 17, wherein the isolating in step (b) comprises centrifuging the reaction mixture and harvesting a nucleic acid-comprising supernatant.

22. The method of claim 17, further comprising after step (c), detecting or characterizing the nucleic acid.

23. A method for efficient separation by flocculation of a contaminant or inhibitor from a nucleic acid-comprising sample, wherein the contaminant or inhibitor inhibits the amplification or hybridization of the nucleic acid in the sample, or inhibits an enzymatic reaction utilizing the nucleic acid in the sample, the method comprising the steps of:
   (a) providing a reaction mixture comprising the sample, a chaotropic agent, ammonium acetate or an equivalent, and a detergent, wherein the presence of the chaotropic agent, the ammonium acetate or equivalent, and the detergent in the reaction mixture with the sample, results in the separation of the nucleic acid and the contaminant, the separation of the nucleic acid and the inhibitor, the separation of a protein present in the sample and the nucleic acid, the separation of a protein present in the sample and the inhibitor, the separation of a protein present in the sample and the contaminant, or any combination of the above, present in the sample;
   (b) isolating the nucleic acid and remaining contaminants and inhibitors from the reaction mixture in a supernatant; and
   (c) contacting the nucleic acid supernatant with a flocculant resulting in the further removal of the contaminant or the inhibitor from the supernatant.

24. The method of claim 23, further comprising purifying or isolating the nucleic acid after step (c).

25. The method of claim 23, wherein the sample is an unprocessed, preserved, freshly isolated, crude or unrefined sample.

26. The method of claim 23, wherein the reaction mixture of step (a) is mixed or vortexed.

27. The method of claim 23, wherein the isolating in step (b) comprises centrifuging the reaction mixture and harvesting a nucleic acid-comprising supernatant.

28. The method of claim 23, further comprising after step (c), detecting or characterizing the nucleic acid.

29. A method for maximum recovery of a nucleic acid from a nucleic acid-comprising sample, the method comprising the steps of:
   (a) providing a reaction mixture comprising the sample, a chaotropic agent, ammonium acetate or an equivalent, and a detergent, wherein the presence of the chaotropic agent, the ammonium acetate or equivalent, and the detergent in the reaction mixture with the sample, results in the separation of the nucleic acid and the contaminant, the separation of the nucleic acid and the inhibitor, the separation of a protein present in the sample and the nucleic acid, the separation of a protein present in the sample and the inhibitor, the separation of a protein present in the sample and the contaminant, or any combination of the above, present in the sample;
   (b) isolating the nucleic acid and remaining contaminants and inhibitors from the reaction mixture in a supernatant; and
   (c) contacting the nucleic acid supernatant with a flocculant resulting in the further removal of the contaminant or the inhibitor from the supernatant; and
   (d) recovering the nucleic acid from the nucleic acid-comprising sample.

30. The method of claim 29, further comprising purifying or isolating the nucleic acid after step (d).

31. The method of claim 29, wherein the sample is an unprocessed, preserved, freshly isolated, crude or unrefined sample.

32. The method of claim 29, wherein the reaction mixture of step (a) is mixed or vortexed.

33. The method of claim 29, wherein the isolating in step (b) comprises centrifuging the reaction mixture and harvesting a nucleic acid-comprising supernatant.

34. The method of claim 29, further comprising after step (d), detecting or characterizing the nucleic acid.

35. A method for post-isolation purification and/or amplification of a nucleic acid extracted from an environmental or a biological sample, wherein the isolated nucleic acid does not yield a detectable amplification product in an amplification reaction, and optionally the amplification reaction is a polymerase chain reaction (PCR), comprising the steps of:
   (a) providing a reaction mixture comprising the environmental or biological sample, a chaotropic agent, ammonium acetate or an equivalent, and a detergent,
   (b) isolating the nucleic acid and remaining contaminants and inhibitors from the reaction mixture in a supernatant;
   (c) contacting the nucleic acid supernatant with a flocculant resulting in the further removal of the contaminant or the inhibitor from the supernatant; and
   (d) purifying and/or amplifying the nucleic acid.

36. The method of claim 35, wherein the sample is an unprocessed, preserved, freshly isolated, crude or unrefined sample.

37. The method of claim 35, wherein the reaction mixture of step (a) is mixed or vortexed.

38. The method of claim 35, wherein the isolating in step (b) comprises centrifuging the reaction mixture and harvesting a nucleic acid-comprising supernatant.

39. A kit executing the method of for isolating a nucleic acid from a sample as described in claim 1 comprising:
   (a) a chaotropic agent;
   (b) ammonium acetate or an equivalent;
   (c) a flocculant;
   (d) a salt solution;
   (e) an ethanol based wash solution;
   (f) a low salt buffer, wherein optionally the buffer comprises Tris EDTA or water;
   (g) a spin filter or spin filters; and
   (h) a collection tube or collection tubes.

40. The kit of claim 39, further comprising a detergent or a surfactant, wherein optionally the detergent is selected from the group consisting of sodium dodecyl sulfate (SDS), sarkosyl, sodium lauryl sarcosinate, cetyltrimethyl ammonium bromide (CTAB), cholic acid, deoxycholic acid, benzamidotaurocholate (BATC), octyl phenol polyethoxylate, polyoxyethylene sorbitan monolaurate, tert-octylphenoxy poly(oxyethylene)ethanol, polyethylene glycoltert-octylphenyl ether (Triton®X-100), (1,1,3,3-tetramethylbutyl)phenyl-polyethylene glycol (Triton®X-114), and a combination thereof.

41. The kit of claim 39, further comprising a homogenizing material.

42. The kit of claim 41, wherein the homogenizing material comprises a bead.

43. The kit of claim 39, further comprising one or more oligonucleotides or free nucleotides.

44. The kit of claim 43, wherein the one or more oligonucleotides hybridize to a nucleic acid from a microorganism, an animal, a plant, an insect, a yeast, a virus, a phage, a nematode, a bacteria, a fungi, a bacterial toxin, or a fungal toxin.

45. The kit of claim 43, wherein the one or more oligonucleotides hybridize to a nucleic acid from:
   (a) a *Bacillus* spp., a *Clostridium* spp., a *Sporolactobacillus* spp., a *Sporocarcina* spp., a *Filibacter* spp., a *Caryopha-*

*num* spp., a *Desulfotomaculum* spp., a *Corynebacterium* spp., a *Micrococcus* spp., a *Mycobacterium* spp., a *Nocardia* spp., a *Peptococcus* spp., a *Peptostreptococcus* spp.; or (b) a nucleic acid from a Gram negative bacteria selected from the family consisting of Acetobacteriaceae, Alcaligenaceae, Bacteroidaceae, Chromatiaceae, Enterobacteriaceae, Legionellaceae, Neisseriaceae, Nitrobacteriaceae, Pseudomonadaceae, Rhizobiaceae, Rickettsiaceae and Spirochaetaceae; or (c) a nucleic acid from *B. anthracis, A. globiformis, B. subtilis, C. renale, C. difficile, M. luteus*, or *R. eryrhropolis*; or (d) a nucleic acid from a variola, a varicella, a reovirus, a retrovirus, HIV, HIV-1, HIV-2, a viral hemorrhagic fever, Ebola, Marburg, Machupo, Lassa, *Variola major*, or viral encephalitis.

46. The kit of claim 43, wherein the free nucleotides are sufficient to carry out a PCR reaction, a rolling circle replication, a ligase-chain reaction, or a reverse transcription reaction.

47. The kit of claim 46, wherein the enzyme is a polymerase.

48. The kit of claim 39, further comprising at least one enzyme.

* * * * *